(12) United States Patent
Goyal et al.

(10) Patent No.: US 7,785,850 B2
(45) Date of Patent: Aug. 31, 2010

(54) **HETEROLOGUS EXPRESSION OF TRYPANOTHIONE REDUCTASE FROM *LEISHMANIA DONOVANI* IN A PROKARYOTIC SYSTEM**

(75) Inventors: Neena Goyal, Lucknow (IN); Mukul Kumar Mittal, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 594 days.

(21) Appl. No.: 10/996,174

(22) Filed: Nov. 23, 2004

(65) Prior Publication Data

US 2006/0110791 A1  May 25, 2006

(51) Int. Cl.
*C12N 9/02* (2006.01)
*C12N 1/20* (2006.01)
*C12N 15/00* (2006.01)
*C07H 21/04* (2006.01)
*C07H 21/02* (2006.01)
*C12Q 21/04* (2006.01)
*C12Q 1/68* (2006.01)
*C12Q 1/00* (2006.01)
*C12Q 1/26* (2006.01)

(52) U.S. Cl. ............... 435/189; 435/4; 435/6; 435/69.1; 435/71.1; 435/252.3; 435/320.1; 435/440; 435/25; 536/23.2; 536/23.1

(58) Field of Classification Search ........... None
See application file for complete search history.

(56) References Cited

OTHER PUBLICATIONS

Branden et al. (Introduction to Protein Structure, Garland Publishing Inc., New York, p. 247, 1991.*
Addgene Catalog. pET41a. (2003-2007).*
Promega Catalog. pGEM-T. (1998).*
Novagen—pET-41a-c(+) Vector—1999.*
Sambrook et al. Molecular Cloning, 1989, Cold Spring Harbor Laboratory Press, pp. 8.46-8.52 and pp. 11.2-11.19.*
Goyal et al.—EMBL Accession No. AJ 415162. Oct. 2001.*
Taylor M.C. et al, The structure, organization, and expression of the *Leishmania donovani* gene encoding trypanothione reductase, Molecular and Biochemical Parasitology, 1994, 64(2), pp. 293-301.
Sullivan F.X. et al, Expression of trypanosoma congolense trypanothione reductase in *Eschericia coli*: overproduction, purification, and characterization, Biochemistry, 1989, 28, pp. 4986-4992.
Sullivan F.X. and Walsh C.T., Cloning, sequencing, overproduction, and purification of trypanothione reductase from *Trypanosoma cruzi*, Molecular and Biochemical Parasitology, 1991, 44(1), pp. 145-147.
Castro-Pinto D.B. et al, Cloning and expression of trypanothione reductase from a New World Leishmania species, Archives of Microbiology, 2008, 189(4), pp. 375-384.

* cited by examiner

*Primary Examiner*—Yong D Pak
(74) *Attorney, Agent, or Firm*—McDonnell Boehnen Hulbert & Berghoff LLP

(57) ABSTRACT

The present invention relates to a process for heterologous expression and large-scale production of functionally active enzyme trypanothione reductase of *Leishmania donovani* in prokaryotic system.

32 Claims, 11 Drawing Sheets

Fig.1: Polymerase chain reaction amplification of *Leishmania donovani* Trypanothione Reductase

```
  1 atgtcccgcg cgtacgaccc cgtggtgctt ggcgccggat ctggaggtct ggaggcggga tggaacccgg ccgtcacgca caaaaagaag gtcgggccgt cgtcgatgtg caggcgacgc
121 acggtccgcc gctcttcgct cggcggcacg tgcgtgaacg tcggctgcgt gccaaagaaa ctcatggtga caggtgccca gtacatggac ctgatccgtg agtctggcgg cttcggatgg
241 gagatggacc gcgaatcgct ctgccccac tggaagaagc tcatcgccgc gaagaacaag gtggtgaaca gcatctacga gagctacaag agcatgttcg ctgatacgga gggcctcagc
361 tttcacatgg gcttcggtgc catcaatacg ctcacccggt ggtggtgcgc aagtcggaag accacacag cgacgtgctg ggaccctcga cacggattac atcctcattg ccaccggctc
481 ttggccgacg cgcctcggag tccccggcga cgagttctgc atcacgagca acgaggcttc tacctcgagg atgccccaa gcggatgctg tgcgtcggcg gctgctacat cgccgttgag
601 tttgccggca tcttcaacgg ctacaagccc cagggtgget atgtcgacc gtgctacgc ggcgatctta ttttgcgcgg cttcgataca gaggtgcgca agagcctgac gaagcagctg
721 ggggcgaacg gaataagagt gcgtacaaac ttgaaccga cgaagatcac gaagaatgag gacggctga atcacgttca cttcaacgat ggcacggagg aggactacga tcaggtcatg
841 ctcgcgatcg gtcgcgtgcc gcgctcgcag gcactacagc tcgccaaggc cggcgtccga acaggaaaga acggtgccgt gcaggtcgac gcgtattcga agacatcggt ggacaacatc
961 tacgccatcg ccatcggcga cgtgacgaac cgcgtgatgt tgacgccggt ggccatcaac ganggcgccg ccttcgttga aaccgtcttc ggtggcaagc ccgcgccac cgaccacagg
1081 aaggtcgcgt gccgcgtgtt ctccataccg ccgatcggca cgtgcggcat gaccggaggag gaggcggcga agaactacga aaccgtcgcc gtgtacgcga gctcttttcac gccccttatg
1201 cacaacatca gcggcagcaa gcacaaggaa ttcaagatcc gcatcatcac gaacgaatcc aacggcgagg ttctgggtgt tcacatgctc ggcgacagtg cgcctgagat catccagagc
1321 gtcggcattt gcatgcagat gggcgccaag atcagcgget tccacagcac catcggagtc cacccgacga gcgccgagga gctctgctcc atgcgcacte cagcgtactt ctacgagagt
1441 ggcaagcgcg tcgaaaagct cagcagcaac ctctgaagag ggaggagaga tgaagaagaa
1501 cgcgtcaa
```

Fig.2:*Leishmania donovani* Trypanothione Reductase Nucleotide Sequence (AJ 415162)

```
MSRAYDLVVLGAGSGGLEAGWNPAVTHKKKVGPSSMCRRRTVRRSSLGG
TCVNVGCVPKKLMVTGAQYMDLIRESGGFGWEMDRESLCPHWKTLIAAKN
KVVNSIYESYKSMFADTEGLSFHMGFGAINTLTRWWCASRKTHTATCWDPR
HGLHPHCHRLLADAPRSPRRRVLHHEQRGFYLEDAPKRMLCVGGCYIAVEF
AGIFNGYKPQGGYVDLCYRGDLILRGFDTEVRKSLTKQLGANGIRVRTNLNP
TKITKNEDGSNHVHFNDGTEEDYDQVMLAIGRVPRSQALQLAKAGVRTGKN
GAVQVDAYSKTSVDNIYAIAIGDVTNRVMLTPVAINEGAAFVETVFGGKPRAT
DHRKVACRVFSIPPIGTCGMTEEEAAKNYETVAVYASSFTPLMHNISGSKHK
EFTIRIITNESNGEVLGVHMLGDSAPEIIQSVGICMQMGAKISGFHSTIGVHPT
SAEELCSMRTPAYFYESGKRVEKLSSNL
```

Fig.3: *Leishmania donovani* Trypanothione Reductase deduced amino acids Sequence (AJ415162)

```
LV9  -MSRAYDLVVLGAGSGGLEAGWNAAVTHKKKVAVVDVQATHGPPALVALGGTCVNVGCVP   59
LMA  -MSRAYDLVVLGAGSGGLEAGWNAAATTKKKVAVVDVQATHGPPFFAALGGTCVNVGCVP   59
DD8  -MSRAYDLVVLGAGSGGLEAGWNPAVTKKKEVGPSSMCRRRTVRRSSLGGTCVNVGCVP    58
CFA  -NSRAYDLVVIGAGSGGLEAGWNAASLHKKRVAVIDLQKHHGPPHYALGGTCVNVGCVP    59
TBU  -MSKIFDLVVIGAGSGGLEAGWNAATLYKKRVAVIDVQTHHGPPHYAALGGTCVNVGCVP   59
TCO  -NSKAFDLVIIGAGSGGLEAGWNAATLYKKRVAVVDVQTVHGPPPFFAALGGTCVNVGCVP  59
TCR  MMSKIFDLVVIGAGSGGLEAAWNAATLYKKRVAVIDVQMVHGPPFPSALGGTCVNVGCVP   60
         *: *** ;;***********.**.*   :**.,    .:    :.    :*************

LV9  FKLMVTGAQYMDLIRESGGPGWEMDRESLCPNWKTLIAAKNKVVHSINESYKSHFADTEG   119
LMA  KKLMVTGAQYMDLIRESGGPGWEMNRESLCPNWKTLIAAKNKVVNGINESYKSHFADTEG   119
DD8  KKLMVTGAQYMDLIRESGGFGWEMDRESLCPEWKTLIAAFNKVVNSIYESYKSHFADTEG   119
CFA  KKLMVTGAHYMDTIRESAGFGWELDRESVRPNWKALIAAKNKAVSGINDSYEGNFADTEG   119
TBU  KKLMVTGAQYMDHLRESAGPGWEFDGSSVKANWKKLIAAKNEAVLDINKSYEGHFNDTEG   119
TCO  KKLMVTGAQYMEQLRESAGPGWEFDASTIKANWKTLIAAKNAAVLDINKSYEDHFKDTEG   119
TCR  FKLMVTGAQYMEHLRESAGPGWEFDRTTLRAEKKKLIAVIDEAVLNINKSYEEHFRDTEG   120
         *********;**;  ;***.*****;;  ;;  ..** ***.*;  .*  .*  .**;  ** ****

LV9  LSFHMGPGALQDAHTVVVRKSEDPHSDVLETLDTEYILIATGSWPTRLGVPGDEFCITSN   179
LMA  LSFHMGPGALQDAHTVLVRKSEDPNSDVLETLDTEYILIATGSWPTRLGVPGDEFCITSN   179
DD8  LSFHMGPGAIN-TLTRWWCASRKTHTATCWDPRHGLHPHCERLLADAPRSPRREVLHHEQ   177
CFA  LTFHQGPGALQDNHTVLVRESADPNSAVLETLDTEYILLATGSWPQHLGIEGDDLCITSN   179
TBU  LDFPLGWGSLESKNVVVVRETADPKSAVKERLQADHILLATGSWPQMPAIPGVEHCISSN   179
TCO  LEFPLGWGALEQKNVVTVREGADPKSKVKERLQAEHIIIATGSWPQMLKIPGIEHCISSN   179
TCR  LEFPLGWGSLESKNVVNVRESADPASAVKERLETENILLASGSWPHMPNIPGIEHCTSSN   180
         *  *.  *;;*;;;  .     ..  :  .     -      . :

LV9  EAFYLEDAPKRMLCVGGGYIAVEFAGIFNGYKPCGGYVDLCYRGDLILRGFPDTEVRKSLT  239
LMA  EAFYLEDAPKRMLCVGGCYIAVEFAGIFNGYKPRGGYVDLCYRGDLILRGFDTEVRKSLT  239
DD8  RGFYLEDARKRMLCVGGCYIAVEFAGIFNGYKPQGGYVDLCYRGDLILRGFDTEVRKSLT  237
CFA  EAFYLDEAPKRALCVGGGYISIEFAGIFNAYKARGGQVDLAYRGDMILRGFDSELFKQLT  239
TBU  EAFYLPEPPRRVLTVGGGFISVEFAGIFNAYKPPGGKVTLCYRNMLILRGFDETIREEVT  239
TCO  EAFYLEBPPRRVLTVGGGFISVEFAGIFNAYKPVGGKVTLCYRNNPILPGFDYTLRQBT   239
TCR  EAFYLPEPPRRVLTVGGGFISVEFAGIFNAYKPKDGQVTLCYRGEMILRGFDHTLREELT  240
         ..***  1.*;*  *  ***  ;*;;*******.**  .*  *  *..**.;:  ****** ; *;..*

LV9  KQLGANGIRVRTNLNPTKITKNEDGSNHVHFNDGTEEDYDQVMLAIGVPRSQALQLDKA   298
LMA  KQLGANGIRVRTNLNPTKITKNEDGSNHVHFNDGTEEDYDQVMLAIGRVPRSQTLQLDFA   299
DD8  KQLGANGIRVRTNLNPTKITKNEDGSNHVHFNDGTEEDYDQVMLAIGRVPRSQALQLAKA   297
CFA  EQLRANGINVRTHENPAKVTKNADGTRHVVFESGAEADYDVVMLAIGRVPRSQTLQLDFA   299
TBU  KQLTANGIEIMTNENPAKVSLNTDGSKHVTFESGKTLDVDVVMMAIGRIPRTNDLQLGHV   299
TCO  KQLVANGIDIMTNENPSKIEDIFDGSKHVTFESGKTLDVDVVMMAIGPLPRTGYLQLQTV   299
TCR  KQLTANGIQILTKENPAKVELNADGSKSVTFESGKFMDPDLVMMAIGRSPRTKDLQLQNA   300
         ;** ****  ;  *;  **;*;    * **;.  *  *;.*      *  *  **;***       **;        ***  ..

LV9  GVRTGKNGAVQVDAYSKTSVDNIY--AIGDVTNRVMLTPVAINEGACVLLETVFGGKPPA   356
LMA  GVQTAFNGAVQVDAYSKTSVDNIY--AIGDVTNRVMLTPVAINEG-AAFAETVFGGKFRA   356
DD8  GVRTGKNGAVQVDAYBKTSVDNIYAIAIGDVTNRVMLTPVAINEGAAFVETVFGGKPRA   356
CFA  GVEVAFNGAIKVDAYSKTNVDNIY--AIGDVTDRVMLTPVAINEG-AAFVDTVPANKPRA   356
TBU  GVKLTPKGGVQVDEFSRTNVPNIY--AIGDITDRLMLTPVAINEG-AALVDTVPGNKPRK   356
TCO  GVNLTDKGAIQVDEFSRTNVPNIY--AIGDVTGRIMLTPVAINEG-ASVVDTIPGSKPRK   356
TCR  GVMIK-NGGVQVDEYSRTNVSNIY--AIGDVTNRVMLTPVAINEA-AALVDTVPGTNPRK   356
         **       ;*.;;**  ;*;*.*  ***;  ****;*.*;********.  . . . ;*;*. ;**

LV9  TDHTKVACAVPSIPPIGTCGNTEEEAAKNYETVAVKSSPTPLMHNISGSKHKEFMIRII   416
LMA  TDHTKVACAVPSIPPIGTCGNTEEEAAKNHETVAVYESCFTPLMHHISGSKHKEFMIRII   416
```

Fig. 4 continued

```
DD8  TDHRKVACRVFSIPPIGTCGMTREEAAKNYETVAVYASSFTPLMHNISGSKHKEFTIRII  416
CFA  TDHTKVACAVFSIPPMGVCGYVEEDAAKKYDQVAVYESSFTPLMHNISGSTYKKFMVRIV  416
TBU  TDHTRVASAVPSIPPIETCGLIEEVAAKEFEKVAVYMSSFTPLMHNISGSKYKKFVAKIV  416
TCO  TDHTRVASAVPSIPPIGTCGLTEEEAAKSFEKVAVYLSCFTPLMHNISGSKYKKFVAKII  415
TCR  TDHTRVASAVPSIPPIGTCGLIEEVASKRYEVVAVYLSSFTPLMHNISGSKYKTFVAKII  416
     ***  :**. ******:*.**   ** *:*  .: **** *.************ .:* *   :*:

LV9  TNESNGEVLGVHMLGDSAPEIIQSVGICMKMGAKISDFHSTIGVHPTSAEELCSMRTPAY  476
LMA  TDQPSGEVLGVHMLGDSAPEIIQSVGICMKMGAKISDFHNTIGVHPTSAEELCSMRTPAY  476
DD8  TNESNGEVLGVHMLGDSAPEIIQSVGICMQMGAKISGFHSTIGVHPTSAERLCSMRTPAY  476
CFA  TNHADGEVLGVHMLGDSSPEIIQSVAICLKMGAKISDFYNTIGVHPTREELCSMRTPAY  476
TBU  TNHSDGTVLGVHLLGDGAPEIIQAVGVCLRLNAKISDFYNTIGVHPTSAEELCSMRTPSY  476
TCO  TDHGDGTVVGVHLLGDSSPEIIQAVGICMKLNAKISDFYNTIGVHPTSAEELCSMRTPSH  476
TCR  TNHSDGTVLGVHLLGDNAPEIIQGVGICLKLNAKISDFYNTIGVHPTSAEELCSMRTPSY  476
     *:. .* *:***:***.:*****.*.:%::.****.*:.***************** ::

LV9          FYESGKRVEKLS-SNL  491
LMA          FYENGKRVEKLS-SNL  491
DD8          FYESGKRVEKLS-SNL  491
CFA          FYQKGKRVEKID-SNL  491
TBU          YYLKGEKMETLPESSL  492
TCO          YYIKGEKMETLPDSSL  492
TCR          YYVKGEKMEKPSEASL  492
             :*  .*::*.    :.*
```

Fig. 4 Clustalw linear alignment of TR ORF amino acid sequence of *L. donovani* (Dd8) with other TR sequences of different origin (LV9-*L. donovani* LV9 strain; LMA- *L. major*; DD8- *L. donovani* Dd8; CFA- *C. fasiculata*; TBU- *T. brucei*; TCO- *T. congolense*; TCR- *T. cruzi*.

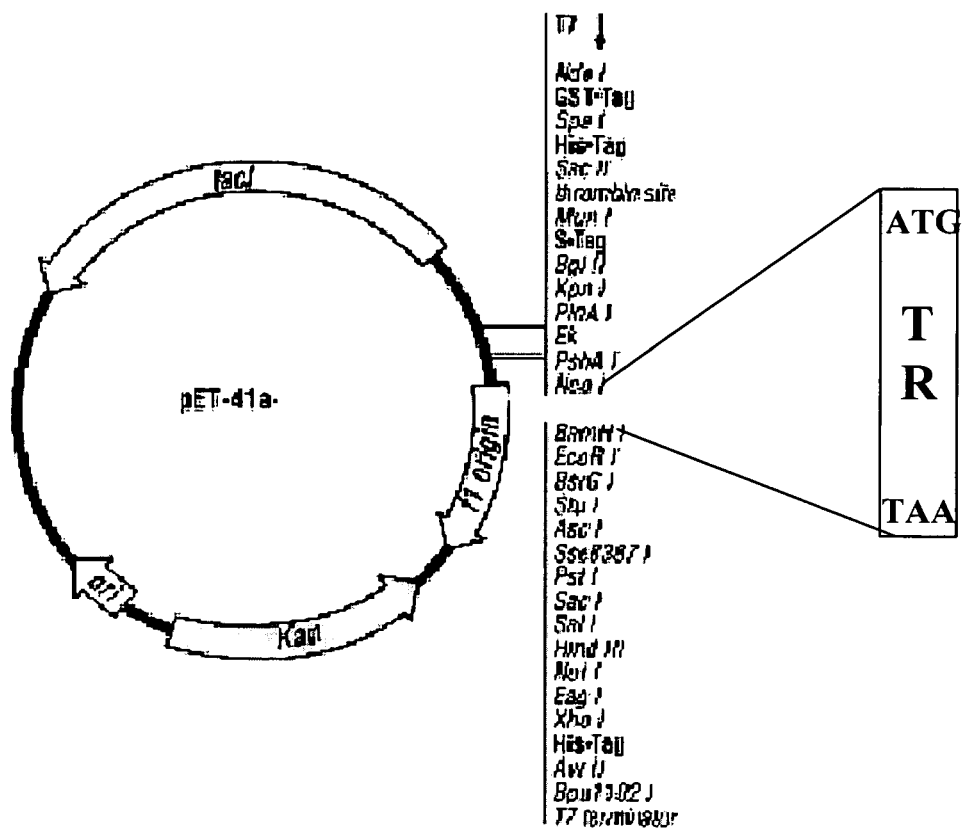
Fig.5: pET 41a + TR Construct

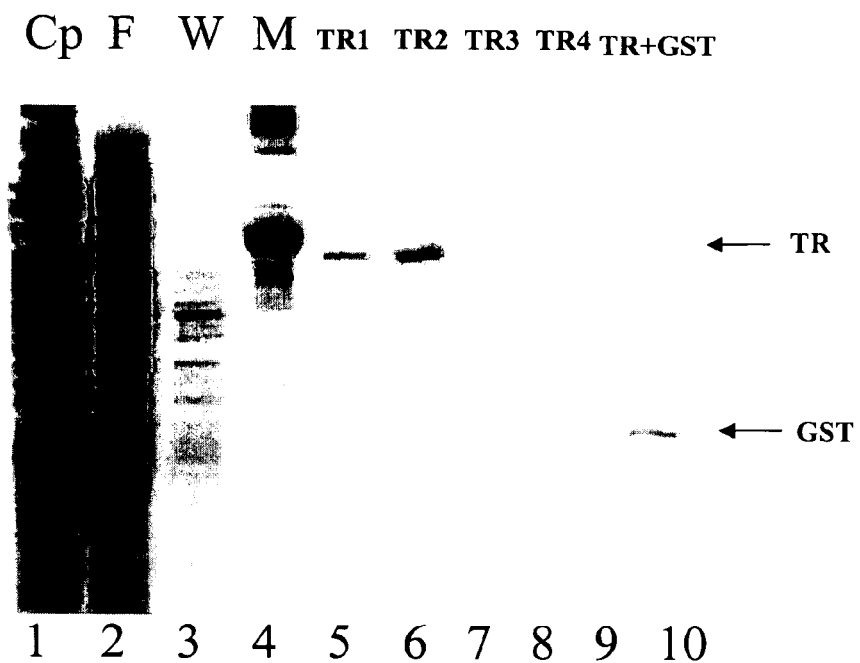
Fig.6: SDS-PAGE analysis of purified Leishmania donovani Trypanothione Reductase

| Lysate | Vol. (ml) | Total Protein mg / 100ml | Totalactivity IU | Specific activity | Purification (X fold) |
|---|---|---|---|---|---|
| Crude | 5 | 37.9 | 4.76 U/ml | 0.634 | 1 |
| Purified | 5 | 1.583 | 3.96 U/ml | 12.53 | 20 |

**Fig.7: Purification of *Leishmania donovani* Trypanothione reductase**

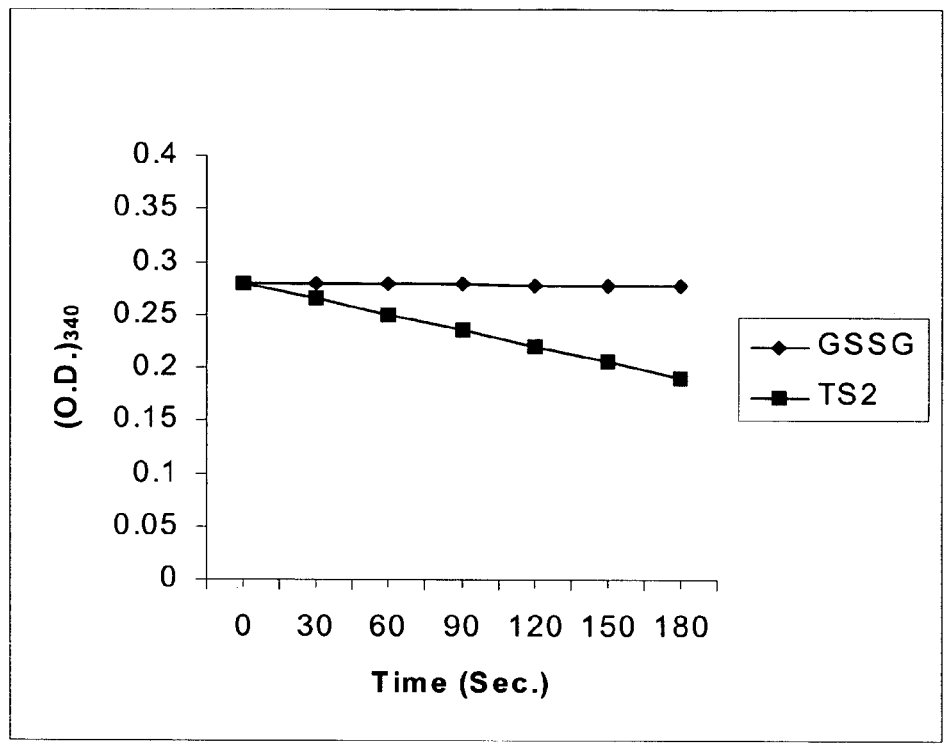
Fig.8:Substrate specificity of purified recombinant *Leishmania donovani* Trypanothione Reductase

|  | $K_m$ (μM) | $V_{max.}$ (μM/ml/min.) |
|---|---|---|
| $TS_2$ | 50 | 200 |
| NADPH | 20 | 125 |

Fig.9: Trypanothione reductase kinetics

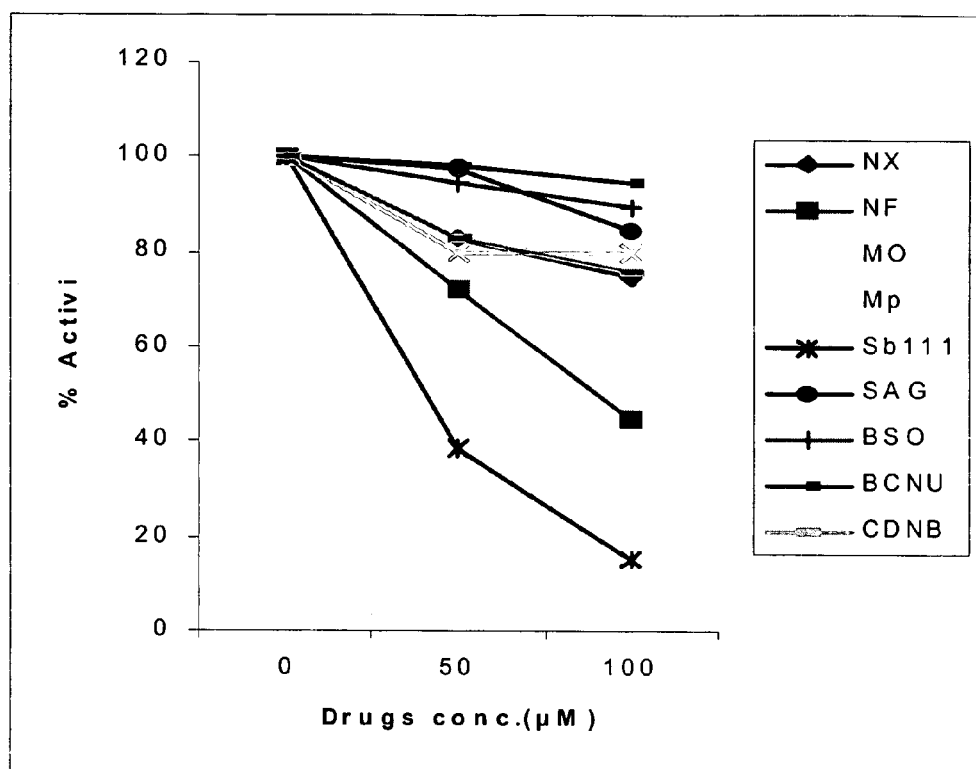
Fig.10:Effect of inhibitors upon *L.donovani* TR activity

US 7,785,850 B2

HETEROLOGUS EXPRESSION OF TRYPANOTHIONE REDUCTASE FROM LEISHMANIA DONOVANI IN A PROKARYOTIC SYSTEM

FIELD OF THE INVENTION

The present invention relates to a process for heterologous expression and large-scale production of functionally active enzyme trypanothione reductase of Leishmania donovani in prokaryotic system.

BACKGROUND INFORMATION

Human leishmaniasis has been rated as the second target next to malaria among the six major diseases identified by the WHO for intensive research and control efforts (1). Leishmania, a trypanosomatid parasite caused a wide spectrum of infection ranging from self-curing ulcer to often-fatal visceral diseases. Further, the disease has been recognized as an opportunistic infection in immunocompromised individuals particularly in patients infected with HIV (2). There is no vaccine in routine use and chemotherapy still relies on antimonial-based drugs, first used in early $20^{th}$ century. The pentavalent antimonials (SbV) drugs Sodium stibogluconate (SAG) and N-methylglucamine antimoniate are the only anti leishmanials chemotherapeutic compounds with a certain degree of efficacy and safety. Sodium stibogluconate (Stibanate) first became available in 1945 (3). Two formulation of pentavalent antimonials are available, sodium stibogluconate solution (Pentosam, Wellcome Foundation, UK) containing 100 mg SbV/ml and meglumine asciculat solution (Glucantine, Rhone Poulence, France) containing 85 mg SbV/ml, and former is used in Indian subcontinent. Currently recommended dose of SbV is 20 mg/kg/day (MKD) for 30 days (4). The drug can be used via intramuscular or intravenous route. Response to relatively small daily dose (600 mg. Max.) for short duration (6-10 days) of SbV had been excellent until the early 1980 (5), when reports of treatment failure appeared, and modifications for SbV treatment were suggested to overcome the drug failure (6). The WHO revised its recommendations twice, resulting in an increase in the daily dose (from 10-20 mg/kg) and duration (from 6-10 days to 20-40 days) (7, 8). However, non-responsiveness to SAG is on increase especially in epidemic areas of visceral Leishmaniasis (9).

Leishmania protein are generally insoluble in nature and tend to form aggregate i.e. inclusion bodies upon expression in prokaryotic hosts e.g. Adenylate kinase 2 of L. donovani (10), Methionine adenosyl transferase (MAT 2) of L. donovani (11), Cysteine protease type A & B (CPA & CPB) genes of L. infantum (12), Glucose regulating protein 94 (GRP 94) of L. infantum (13), Myristoyl-CoA N Myristoyl transferase of L. major (14). To get active protein from inclusion bodies is a tedious process and requires lot of laboratory work and time. Some researchers has worked upon it and tried many conditions to get active protein in the soluble fraction but the yield is too low to work upon this e.g. L. mexicana aminotransferase was expressed to 1 mg./l bacterial culture (15), L. donovani recombinant chitinase Ld CHT1 (16), Ornithine decarboxylase (ODC) was expressed at 0.2% of the soluble protein in E. coli. While Thymidylate synthase dihydrofolate reductase was expressed at a level of 2% of the soluble protein in E. coli. (17). The soluble functionally active enzyme must be substrate specific and should have other kinetic parameters in accordance with the natural enzyme. Therefore, a process needs to be developed for large-scale heterologous expression and purification of functionally active leishmanial proteins. Also, there is an increasing failure of insecticides to control vector. This has led to research on the basic studies to evaluate the significant differences between host and parasite, which leads to development of logical approaches towards new chemotherapeutic agents and vaccines. To validate new targets as well as new molecules active against the parasite requires lot of native target enzyme thereof and it is therefore necessary to get the target enzyme/protein in large amount by developing a heterologus expression system.

As parasites, the trypanosomatids are inevitably exposed to various reactive oxygen species, such as superoxide radicals, hydrogen peroxide and myeloperoxidase products generated during the host defense reaction. However there ability to cope with such oxidative stress appears to be surprisingly weak. They lack both catalase & peroxidase and totally dependent upon unique Trypanothione reductase redox system to overcome this stress. Trypanothione Reductase (TR) is an NADPH-dependent flavoprotein oxidoreductase central to thiol metabolism in the leishmanias and trypanosomatids (18). The uniqueness of this cascade of oxidoreductase offers an opportunity to inhibit the parasite metabolic pathway without causing adverse effects in the host organism therefore make this enzyme an attractive target site for the development of the antileishmanials.

The importance of trypanothione and trypanothione reductase in defending trypanosomatids against nitrosative and oxidative stress was established by disabling the function of trypanothione reductase gene by gene disruption. A double knock out of TR gene in Leishmania species could not be achieved which indicated that null mutants are not viable hence proved importance of the gene in parasite survival (Dumas, C., Quellette, M., Tovar, J., Cunningham, M. L., Fairlamb, A. H., Tamar, S., Olivier, M. and Papadopoulou, B. (1997), EMBO J., 16, 2590-2598). Mutants in which the TR activity had been reduced to half that of wild type by disrupting one member of allelic pair were not able to survive in macrophages that were capable of respiratory burst.

In another approach which relies on the fact that the active enzyme is dimeric in nature an expression vector was constructed bearing inactive mutant of T. cruzi TR gene. This expression construct was heterologously expressed in L. donovani. In the resultant recombinants, a large proportion of the TR consisted of inactive heterodimer with the result that TR activity was reduced to approximately 15% of normal cells (Tovar, J., Cunningham, M. L., Smith, A. C., Croft, S. L. and Fairlamb, A. H. (1998) PNAS, 95, 5311-16). These recombinant *L. donovani* cells expressing very less active TR were incapable of surviving in IFN-gamma activated macrophages. This further confirms that parasite with much less TR activity than wild type were more vulnerable to oxidative and nitrosative stress".

Heterologous expression means the expression of a gene from one organism into another organism. In the paper by Tovar et al, 1998, an inactive mutant of *T. cruzi* TR was expressed in *L. donovani* cells resulting recombinant *Leishmania* cells expressing inactive TR. While, we have expressed the Leishmanial TR gene in *E. coli* cells resulting recombinant bacterial cells expressing active Leishmanial TR which was not done before. These recombinant bacterial cells were used to purify Active Leishmanial enzyme. Though in both cases the expression of TR was heterologous but in first case it was expression of inactive mutant TR of *T. cruzi* in *L. donovani* while in second it was expression of active *L. donovani* TR in *E. coli* cells.

The main objective of this patent is to get *L. donovani* TR in very high yield and at very low cost. This was achieved by expressing *L. donovani* TR in *E. coli* bacterial cells. The enzyme can be purified from the parasite itself but the process is very expensive, cumbersome therefore time consuming. Moreover the yield was very low [Cunningham, M. L. and Fairlamb, A. H. (1995) Eur. J. Biochem., 230, 460-468]. To grow one liter of promastigotes of *L. donovani* in liquid 199 medium involves an expenditure of approximately $57.00 which will generate approximately 2.5 g parasite while to grow 1 L bacterial culture that comes only $1.69 generating 12.5 g cells. Further purification steps to process 1 L parasite culture will cost $ 1011.8 resulting in total yield of only 0.47 mg protein while purification from bacterial 1 L culture will cost only 131$ with a total yield of approximately 16 mg protein (Table).

The expression vectors used in the present study have far more advantage in obtaining the desired results as revealed by the present study. In addition to pET41a we tried four more expression vectors but the yield of active protein was very-very less. Almost all of the expressed protein was inactive in the form of inclusion bodies. The best yield of the active recombinant Leishmanial TR was observed with pEt41a vector expressing in *E. coli* cells strain BL21.

So far Trypanothione reductase has been isolated from *C. asciculate* itself (19) and from *Trypanosoma cruzi* (2.2 mg. TR/33 g wet weight of cultured epimastigotes) (20). Briefly, 33.4 g cells were suspended in 100 ml of buffer A (50 mM Potassium phosphate, 1 mM EDTA, pH7.0 at 25° C.) in presence of 1 mM digitonine. After 10 min. of gentle stirring the suspension was freeze thawed for 2 cycles and centrifuged for 30 min at gravitational force, 4000 g and temperature 4° C. The supernatant was combined with 50 ml of 2'5' ADP sepharose pre-equilibrated with buffer A. The suspension was shaken for 2 h and transferred to a chromatography column. Column was washed first with 150 ml of buffer A (at 4° C.) followed by 60 ml of buffer B (RT) TR was eluted using 75 ml of 0.3 mM NADPH in buffer B. Active fractions were combined to give TR in 2 electron-reduced form (EH2) which is susceptible to nonspecific auto oxidation. TR (EH2) was reduced by addition of $TS_2$ and GSSG to a final conc. Of 1.6 μM and 1 mM respectively. Reaction was allowed to proceed for 30 min. at 25° C. resulting in fraction 2. Fraction 2 was applied on to DEAE sephadex A-50 column pre-equilibrated with buffer B. Column washed with buffer B and yellow band of TR was eluted with 0.5M KCl. Active fractions were combined. TR was precipitated with slow addition of solid ammonium sulfate to 60% saturation. After 24 h of precipitation at 4° C. the sample was centrifuged at gravitational force, 6000 g for 10 min at 4° C. temperature. The yellow precipitate was washed thrice with 45% ammonium sulfate in buffer A resulting in 95% pure trypanothione reductase.

In 1989, first time, the cloned TR gene from *Trypanosoma congolens* had been expressed in *E. coli*, where the yield was only 1% of the total soluble fraction of the bacterial cells (17). The cell pellet obtained from 1 L of culture of induced cells were suspended in 25 ml buffer A (20 mM phosphate buffer pH7.2, 5 mM BME, 1 mM EDTA), sonicated six times for 1 min each and centrifuged. Nucleic acids were removed by addition of protamine sulphate to 0.4% concentration. The cloudy solution was then brought to 40% saturation with ammonium sulfate. Precipitated proteins and nucleic acid were removed by centrifugation and TR in supernatant was precipitated with 60% ammonium sulphate. The resulting pellet of TR was dissolved in buffer B (20 mM Tris, 5 mM BME, 1 mM EDTA pH7.2) and dialyzed extensively.

The dialyzed solution was applied to DEAE sephacel (pre-equilibrated) column. The TR was eluted at 0.1M KCl as yellow protein, which was dialyzed against buffer A. The yellow protein solution was applied on to 2'5' ADP sepharose pre-equilibrated column. The column was washed with 100 ml of buffer A and pure TR was eluted with 5 mM $NADP^+$ in buffer A. The enzyme was dialyzed against buffer A and stored at 4° C. after concentration. Thus, the purification process was quite lengthy and involves several steps of purification.

TR from *Trypanosoma cruzi* was cloned and expressed in *E. coli* (21). However, all the steps for the purification of recombinant TR were almost same as described for *T. congolens* (17) with a yield of approximately 6 mg/l bacterial culture.

TR from *L. donovani* Ethiopian strain has been cloned, over-expressed in parasite itself (22). However, purification of the enzyme from overexpressing parasite resulted in very poor yield to work upon (23). No reports are available for heterologous expression of Leishmanial trypanothione reductase in prokaryotic system.

We have presented a comparative data in table 1 which shows the present process is far more advantages than the earlier known methods. Further table 2 shows another comparison cost effectiveness of the present method than the known methods.

TABLE 1

Comparison of the present invention with the prior art

| Source | Vector | Host cells | Purification procedures | Yield |
|---|---|---|---|---|
| *T. congolens* (TR) (ref. 17) | PCGTR-2 | *E. coli* (SG5) | 1. Salt precipitation - 40-60%,<br>2. Anion exchange chromatography - DEAE sephacel,<br>3. Affinity chromatography- 2'5'ADP-sepharose, | 3.2 mg/L bacterial culture |

TABLE 1-continued Comparison of the present invention with the prior art

| Source | Vector | Host cells | Purification procedures | Yield |
|---|---|---|---|---|
| T. cruzi (TR) (ref. 21) | pIBITczTR | E. coli | 1. Salt precipitation - 40-60%, 2. Anion exchange chromatography-DEAE sephacel, 3. Affinity chromatography- 2'5'ADP-sepharose, | 6 mg/L bacterial culture |
| C. fasciculate (Ref. 19) | From parasite | From parasite | 1. Salt precipitation - 40-60%, 2. Anion exchange chromatography - DEAE sephacel, 3. Hydroxyapitite chromatography 4. Affinity chromatography- 2'5'ADP-sepharose, 5. Ultragel | 0.49 mg/L of parasite culture |
| L. donovani (Dd8 strain) (Present invention) | pET-41a | E. coli-BL21 (DE3) | Single step - Glutathione--sepharose affinity chromatography | 16 mg/l bacterial culture |

Comparison of the cost in US$ required to purify 1 mg of LDTR enzyme from 1L. donovani promastigotes and recombinant E. coli cells (Table 2)

TABLE 2

| S. No. | Steps involved in purification of TR | Cost (Parasite L. donovani)US$ | Cost (Bacterial E. coli) US$ |
|---|---|---|---|
| 1. | Culture of 1 L | 57.00 | 1.69 |
| 2. | Purification Process | Three step (two affinity & one size chromatography) cost = 1011.80 | Single(affinity chromatography Cost = 131.00 |
| 3. | Time (from culture to purification) | 12 days | 2.5 days |
| 4. | Yield of Enzyme | 0.47 | 16 mg |
| 5. | Cost/mg protein | 1239.00 | 8.29 |

OBJECTS OF THE INVENTION

The main object of the present invention provides a process for heterologus expression and large-scale production of functionally active enzyme trypanothione reductase of Leishmania donovani in prokaryotic system.

Another object of the present invention provides characterization of the protein and that they can be prepared by means of and/or isolated from a species of the family Trypanosomatidae.

Still another object of the present invention provides a prokaryotic expression system for the expression of the said enzyme which is cheapest and easiest for large-scale yield.

Yet another object of the present invention provides expressed recombinant enzyme as biologically active and as a soluble fraction of the total lysate.

One more object of the present invention provides the enzyme in a soluble fraction which requires no further treatment for down stream applications.

Still another object of the present invention provides higher total yield of the purified fraction than the earlier reported methods.

Another object of the present invention provides the purified active enzyme which is stable at low temperature for long periods.

One more objective of the present invention relates use of primers having SEQ ID No.3 and SEQ ID No.4 for isolating Open Reading Frame (ORF) of trypanothione reductase from Leishmania donovani strain Dd8 (available at ATCC no. 50212) and its heterologous expression in a prokaryotic system.

Yet another object of the present invention relates to a use of cloning and expression vectors for cloning Open Reading Frame (ORF) of trypanothione reductase of Leishmania donovani strain Dd8 and its heterologous expression in a prokaryotic system.

Still another object of the present invention relates to obtain L. donovani TR in very high yield and at very low cost by expressing L. donovani TR in E. coli bacterial cells

BRIEF DESCRIPTION OF ACCOMPANYING FIGURE/DRAWINGS

FIG. 1. describes the PCR amplification of Leishmania donovani Trypanothione reductase ORF using L. donovani genomic DNA as a template:

Lane 1-4: Different concentration of L. donovani genomic DNA

Lane 5-7: Master mix

Lane 8: Molecular weight marker {100 bp ladder (GIBCO BRL)}

FIG. 2. describes the nucleotide sequence of cloned Leishmania donovani Trypanothione reductase of L. donovani (SEQ ID No. 1).

FIG. 3. describes the amino acid sequence encoded by cloned Leishmania donovani Trypanothione reductase (SEQ ID No. 2).

FIG. 4. describes the sequence alignment of Leishmania donovani Trypanothione reductase (DD8; SEQ ID No. 2) with other known Trypanothione Reductase sequences (LV9—L. donovani HU3 strain (EMBL Accession No. Z23135.1), SEQ ID No. 7; LMA—L. major (EMBL Accession No. CT005244.1), SEQ ID No. 8; CFA—C. fasiculata (EMBL Accession No. Z126118.1), SEQ ID No. 9; TBU—T. brucei (EMBL Accession No. X63188.1), SEQ ID No. 10; TCO—T. congolense (DB source TRBTRTR Accession No. M21122.1), SEQ ID No. 11 and TCR—T. cruzi (EMBL acc. No. Z13958.1), SEQ ID No. 12).

FIG. 5. describes the *Leishmania donovani* Trypanothione Reductase construct in pET 41a expression vector.

FIG. 6. describes the SDS PAGE analysis of expressed *Leishmania donovani* Trypanothione Reductase and purified recombinant *Leishmania donovani* Trypanothione Reductase under reducing conditions on 10% gel.
Lane 1: Cp—Crude *E. coli* supernatant
Lane 2: F—Flow through
Lane 3: W—Wash 2
Lane 4: M—BSA (marker)
Lane 5-7: $TR_{1-4}$, 54.6 Kd purified fractions
Lane 8: TR and GST fractions FIG. 7. describes the fold purification of Recombinant *Leishmania donovani* Trypanothione Reductase.

FIG. 8. describes the substrate specificity of recombinant purified *Leishmania donovani* Trypanothione Reductase. GSSG-Oxidised Glutathione, $TS_2$-Oxidised Trypanothione FIG. 9. describes the kinetics of Trypanothione Reductase with NADPH and trypanothione.

$K_m$—Michelies-Menten constant, $V_{max.}$—Max. Velocity, $TS_2$—Oxidized Trypanothione, NADPH—Nicotinidine adenine dinucleotide phosphate FIG. 10. describes the effect of inhibitors on TR activity (NX—Nifurtimox, NF—Nitrofurazone, MO—Melarsen oxide, MP—Melarsoprol, SbIII—Potassium antimony tartrate, SAG—Sodium antimony gluconate, BSO—DL-Buthionine-sulfoximine, BCNU—carmustine, CDNB—1 chloro, 2-4dinirobenzene)

SUMMARY OF INVENTION

Heterologous expression denotes expression of a gene isolated from one organism/cells into another (different) organisms/cells to get large amount of the expressed protein. Selected organism should express the protein not only in large amount but also in functional form. The three available systems used for heterologous expression are bacterial, yeast and mammalian cells. Most preferred is bacterial system. Trypanothione reductase(TR)enzyme of any *Leishmania* species has not been heterologously expressed in bacterial system due to various limitations described in prior art (Table 1). For the first time expression TR enzyme of *L. donovani* (in functionally active form) in *E. coli* expression system is reported.

Primers were designed to pull out TRORF from *L. donovani* genome using PCR, which were novel and have not used before therefore non-obvious.

The expression vector used in this invention, pET 41a, has His and GST tags. This vector has not been used before for the expression of TR of even any other trypanosomatid parasite including *Leishmania*. Therefore selection of the vector was novel and non-obvious from the literature.

Protein is expressed as fusion protein with GST, which helps in expression of protein in soluble form as well as reduces conventional several step purification processes to single step. GST could be cleaved onto column so the protein could be obtained in single band form even in first elution. Use of this vector for expression of TR has made the purification process very easy and has reduced time and chemical consuming lengthy process to single step. This is the novelty of the invention.

Conditions are developed to get more than 80% expression of recombinant enzyme/protein in soluble form. Temperature of the culture, concentration of IPTG (isopropyl-D-thiogalactopyranoside) and time of induction play most important role in solublization of enzymes/protein in prokaryotic expression. So far studies reported maximum 10-20% of the total protein expressing in soluble form. This invention has developed the conditions, which resulted in more than 80% expression of TR enzyme in soluble form which are again novel and non-obvious.

Simple steps for the maximum binding and elution of recombinant enzyme/protein from the column are defined that are not obvious from the prior art and are therefore novel.

DETAILED DESCRIPTION OF THE INVENTION

The present invention provides a process for heterologus expression and large scale production of functionally active enzyme trypanothione reductase of *Leishmania donovani* in prokaryotic system, which comprises; (a) amplification of open reading frame of trypanothione reductase of strain Dd8 (WHO ref no MHOM/IN/80/Dd8) ATCC No 50212, causative agent of Indian Kala azar, using polymerase chain reaction; (b) cloning of the amplified product (Ld TR ORF) in TA cloning vector, sequence analysis of cloned TR; (c) subcloning of LdTRORF in prokaryotic expression vector; (d) development of experimental conditions for maximum expression of cloned LdTRORF in soluble native form; (e) purification of the enzyme to homogeneity using affinity chromatography; (f) analysis of fold purification and specific activity; (g) biochemical characterization to determine Vmax and Km and (h) effect of known TR inhibitors, thiol depletors and antileishmanial drug(s) on recombinant purified Ld TR.

Accordingly, the main embodiment of the present invention relates to a process for heterologous expression of active enzyme trypanothione reductase of *Leishmania donovani* strain Dd8 (available at ATCC no. 50212) in a prokaryotic system, said process comprising the steps of:

(a) amplifying, identifying and isolating the Open Reading Frame (ORF) of trypanothione reductase having DNA SEQ ID No. 1 and corresponding protein SEQ ID No. 2 using forward primer having SEQ ID No. 3 and reverse primer having SEQ ID No. 4,
(b) cloning of the amplified product of step (a) in cloning vector,
(c) subcloning of the amplified product of step (b) in expression vector,
(d) transforming the cloned ORF of steps (b) & (c) in a prokaryotic system,
(e) studying the expression of the ORF transformed in step (d) under different in vitro conditions, and
(f) purifying the enzyme from step (e) to homogeneity, and
(g) analyzing physical and biochemical properties of the enzyme to establish the heterologous expression of soluble native form of Trypanothione reductase (accession no. ORF AJ415162 of *Leishmania donovani* strain Dd8 WHO ref. no. MHOM/IN/80/Dd8, available at ATCC 50212) in a prokaryotic system.

Another embodiment of the present invention relates to oligonucleotide primers having SEQ ID No.3 and SEQ ID No.4 for isolating Open Reading Frame (ORF) of trypanothione reductase (SEQ ID 1, EMBL accession no. AJ415162) from *Leishmania donovani* strain Dd8 (WHO ref. no. MHOM/IN/80/Dd8) and its heterologous expression in a prokaryotic system.

Yet another embodiment of the present invention relates to selection of cloning and expression vectors for cloning of Open Reading Frame (ORF) of trypanothione reductase from *Leishmania donovani* strain Dd8 and its heterologous expression in a prokaryotic system.

Still another embodiment of the present invention relates to enzyme trypanothione reductase, wherein the enzyme trypanothione reductase, is central to thiol metabolism of the parasite and essential for the survival of the parasite in the macrophage system. Still another embodiment of the present invention relates to enzyme trypanothione reductase, wherein the enzyme trypanothione reductase is a drug target for prevention and treatment of *Leishmania donovani*.

Still another embodiment of the present invention relates the amplification conditions in step (a) are single cycle at 95° C. for 9 min followed by 25 cycles of 95° C. for 1-2 min., 45° C.-47° C. for 1 min. and 72° C. for 2-3 min and final single cycle of 72° C. for 4 min.

Still another embodiment of the present invention relates the complete open reading Frame (ORF) having nucleotide SEQ ID NO.1 and corresponding protein SEQ ID NO.2 isolated in step (a) was amplified using forward oligonucleotide primer having SEQ ID No.3 and reverse oligonucleotide primer having SEQ ID No. 4.

Still another embodiment of the present invention relates the cloning vectors, wherein cloning vectors in step (b) is selected from group comprising of pCR-TOPOII, TA, and pGEM-T.

Still another embodiment of the present invention relates to the cloning vector wherein, wherein cloning vector selected is pGEM-T.

Still another embodiment of the present invention relates to a process as claimed in step (a), wherein cloning conditions in step (b) are:

Vector and insert ratio 1:3 (1.5 µl: 4.5 µl; 120 ng of insert DNA),
T4 DNA ligase 1 µl (10 U/µl),
10× phosphate buffer,
Ligation conditions 14° C. for 18 hrs.

Still another embodiment of the present invention relates to a process in step (c), wherein expression vectors in step (c) is selected from group comprising of pQE 30, pET 21d, pET 28b, pET 41a and pGEX4T vectors.

Still another embodiment of the present invention relates to the expression vector, wherein expression vector selected is pET41a.

Still another embodiment of the present invention relates to the prokaryotic system for cloning in step (d) are is from group comprising of JM 109 *E. coli* cells.

Still another embodiment of the present invention relates to prokaryotic expressions in step (d) are selected from group comprising of BL21 DE3 or M-15 *E. coli* cells.

Still another embodiment of the present invention relates to prokaryotic expression system is selected is BL21 DE3 *E. coli* cells.

Still another embodiment of the present invention relates to, wherein the ORF sequence (designated as LDTR or LddTRpET41aDE3) of trypanothione reductase isolated from *Leishmania donovani* strain Dd8 is different from other known such sequences (FIG. 4).

Still another embodiment of the present invention relates to the purification steps in step (f) said purification are as following:

(a) growing the *E. coli* cells containing LdTRORF overnight,
(b) harvesting cells of step (a) and suspending them in lysis buffer,
(c) sonicating the harvested cells and removing the debris from the harvested cells of step (b),
(d) resuspending the cells again in phosphate buffer,
(e) loading the suspended cells of step (d) in pre-equilibrated column of glutathione sepharose 4B column and incubating for about 5 hrs. at 22-20 min,
(f) washing the column during incubation in step (e) twice with chilled PBS buffer, and adding thrombin at concentration of 1 U/100 µg of loaded protein, and
(g) eluting the recombinant enzyme from step (f) by adding 20-25 ml of elution buffer.

Still another embodiment of the present invention relates to growth temperature of *E. coli* cells, wherein the *E. coli* cells are grown at temperature of about 22-27° C.

Still another embodiment of the present invention relates to composition of lysis buffer, wherein the lysis buffer comprises of potassium phosphate buffer (10 mM) pH 7.2, 10 mM EDTA, 0.01% triton X 100, 0.1 mM PMSF Still another embodiment of the present invention relates to the sonication, wherein sonication is done 3-5 times for 30 sec to 1 min pulse with 1-2 min. cooling interval.

Still another embodiment of the present invention relates to the removal debris by centrifugation, wherein the debris is removed by centrifugation at 9000-120000 g from 15-20 min.

Still another embodiment of the present invention relates to the elution buffer, wherein the elution buffer is 50 mM Tris-HCl, pH 8.0.

Still another embodiment of the present invention relates to the recombinant protein (LdTR), wherein the recombinant protein is isolated is having molecular mass of 54.6 kd.

Still another embodiment of the present invention relates to the recombinant protein, wherein recombinant protein is having specific activity of 12.5 U/mg.

Still another embodiment of the present invention relates to the total yield of recombinant protein, wherein the total yield of the recombinant protein is 16 mg/liter.

Still another embodiment of the present invention relates to the $V_{max}$ of recombinant protein, wherein $V_{max}$ of recombinant protein with $TS_2$ is 200 µM/ml/min and with $NADPH_2$ is 125 µM/ml/min.

Still another embodiment of the present invention relates to the $K_m$ pf recombinant protein, wherein $K_m$ of recombinant protein with $TS_2$ is 50 µM and with $NADPH_2$ is 20 µM.

The following examples are given by the way of illustrations and therefore should not be construed to limit the scope of the present invention.

EXAMPLES

Example 1

Cloning and Sequencing of TR of *Leishmania donovani* Dd8 Strain

Cloning and Sequencing:

Trypanothione reductase (TR) gene is a single copy gene in Leishmanial genome and is located on a 1.1 MB chromosome (23). Complete Open reading frame of the said protein was amplified using genomic DNA (100-200 ng/reaction) as a template and primers designed from known sequences flanking the TR ORF. The template DNA was initially denatured at 94° C. for 6-9 min. then allow to amplify using 25-30 cycles at 95° C./1-2 min., 45-47° C./1 min. and 72° C./2-3 min. The purified PCR product was cloned in any TA cloning vector like TOPOII vector (Invitrogen), pGEM-T (Promega) and TA cloning vector of Stratagene. The plasmid was then transformed and propagated in suitable *E. coli* competent cells. In total 5-7 clones were sequenced using dideoxy method (Sanger et al) in both direction to confirm the sequence of the amplicon and a 1508 nucleotide long ORF was submitted in EMBL genesequence (AJ415162). Two different restriction sites were incorporated in forward (TR-ATG) and reverse (TR-TAA) primers for directional subcloning in *E. coli* expression vector. LdTRORF was amplified using these primers. The purified PCR product was digested with restriction enzymes to provide cohesive ends and ligated to suitable expression vector which can be pQE 30, pET 21d, pET 28b, pET41a and in pGEX4T expression vectors. The ligated mixture was first transformed into the suitable (compatible to vector) E. coli competent cells and sequenced the insert. After confirmation of the sequence, the construct was further transformed again into the suitable host expression cells for heterologous expression of the protein. Host cells could be BL21DE3, M-15 or BL21DE3 (p Lys) depending upon the expression vector.

Cell culture and DNA extraction: *L. donovani* promastigotes (WHO ref no MHOM/IN/80/Dd8) ATCC No 50212, regularly maintained at Central Drug Research Institute in Golden hamsters and grown in vitro in NNN medium (26) is used for extraction of genomic DNA. The cells were harvested by centrifugation for 15 min. at 5000 rpm, washed twice with saline (0.9% NaCl) and suspended in 5 ml buffer (0.2M TrisHCl pH 8.0, 0.2M EDTA, 0.5% SDS, 1 mg/ml proteinase K). Cell lysate was incubated for 5 hours at 50° C. and then extracted once with equal volume of phenol chloroform:isoamylaalcohol (25:24:1) by mixing very slowly followed by centrifugation (10,000 rpm×10 min. at 4° C.). Aqueous layer was further extracted once with chloroform: isoamylalcohol (24:1). Genomic DNA was precipitated with sodium acetate (3M, pH 5.2 ($1/10^{th}$ vol. of the aqueous phase) and 2.5 Vol. of absolute ethanol).

Primers, PCR amplification, cloning and sequence analysis: Primers were designed from *L. donovani*, (Ethopian strain) sequences flanking the TR ORF. Forward primer: 5'CTCGCGAAAATTCTTCG3' (SEQ ID No. 5), Reverse primer: 5'GAGATGAAGAAGAAGGGCCTAA3' (SEQ ID No. 6). Polymerase chain reaction was performed using 200 ng of *L. donovani* genomic DNA as template, 45 µl of PCR mix. (Gibco BRL) and 60 ng of each primer. The PCR conditions were 95° C./9 min. (initial), 95° C./1 min., 47° C./1 min. and 72° C./2 min. for 25 cycles and final extension single cycle at 72° C. for 4 min. The amplified product was analyzed by gel electrophoresis. Single band of 1.5 kb was obtained (FIG. 1 describes the PCR amplification of *Leishmania donovani* Trypanothione reductase ORF using *L. donovani* genomic DNA as a template. Lane 1-4 depicts amplification of 1.5 kb LDTR band from different concentration of *L. donovani* genomic DNA). The band was purified from gel using (QIAGEN Gel extraction Kit) and was ligated in pGEMT cloning vector (Promega). Ligation mixture consists of vector and insert in 1:3 ratio, 1.5 µl and 4.5 µl respectively (120 ng DNA), T 4 DNA ligase, 1 µl (10 U/µL, GIBCO BRL), 10× buffer, 1 µl and TDW, 2 µl. The mixture was incubated at 14° C. for 18 hr. 4 µl (around 50 ng DNA) of ligated mixture was transformed and propagated in *E. coli* JM 109 competent cells. Transformed cells were selected by Ampicillin (100 µg/ml) resistance. Plasmids were purified using QIA prep spin plasmid kit (Qiagen Inc.). About 20 µg plasmid DNA was purified from 5 ml of culture. 2 µg (4 µl) of DNA was digested with Not 1(1 µl) in presence of 10× buffer (2 µl) in a total reaction volume of 20 µl and analyzed on 100 agarose gel for the presence of 1.5 kb insert. In total 5 clones were sequenced using dideoxy method (Sanger et al) in both directions to confirm the sequence of amplicon and a 1508 nucleotide long ORF was submitted in EMBL gene sequence (AJ415162). The full length encoding DNA and deduced amino acid sequence is shown in FIG. 2 (the nucleotide sequence of cloned trypanothione reductase of *L. donovani*) and FIG. 3 (the amino acid sequence encoded by cloned *Leishmania donovani* trypanothione reductase). Sequence alignment analysis was performed using Meg-align software of DNA star. FIG. 4 showed Clustalw linear alignment of TR ORF amino acid sequence of *L. donovani* (Dd8) with other TR sequences of different origin (LV9—*L. donovani* HU3 strain; LMA—*L. major*; DD8—*L. donovani* Dd8; CFA—*C. fasciculata*; TBU—*T. brucei*; TCO—*T. congolense*; TCR—*T. cruzi*). The *L. donovani* nucleotide sequence is most similar to Ethopian strain with 96% homology, while *L. major* TR is 92%, *C. fasciculata* 81% *T. congolens* 82% and *T. brucei* is 84% identical. The identity at amino acid level is little lesser and it is 84% with Ethiopian strain, 81% with *L. major*, 68% *C. fasciculata*, 59% with *T. congolens* and 60% with *T. cruzi*.

Example 2

Expression and Purification of Recombinant LdTR Protein to Homogeneity

A single colony of *E. coli* containing LdTRORF was inoculated in to 5-10 ml LB medium with ampicilline (75-100 µg/ml) and kanamycin (50-100 µg/ml) and allowed to grow at 22-37° C. overnight. The overnight grown culture was then transferred to 100 ml LB in 1:50 or 1:100 ratios containing ampicilline (50-100 µg/ml) and kanamycin (50-100 µg/ml) and incubated further at 20° C.-35° C. The culture was grown to the culture density of $(O.D.)_{600}$=0.5-0.8 and induced with 0.1-2 mM IPTG and then incubated at 20-28° C. for 6-18 hrs. The cells were harvested by centrifugation at 3000-5000 rpm for 20 min at 4° C. The wet cell pellet was suspended into 20 ml of lysis buffer (10 mM $K^+Po_4^-$ buffer pH 7.2, 10 mM EDTA, 0.01% tritonX100, 0.1 mM PMSF) and sonicated with a power at 50 W (3-5 times 30 sec to 1 min. pulse with 1-2 minute cooling interval). The cell homogenate was centrifuged at gravitational force 9000-12000 g for 15-20 min. After removing debris clear supernatant was loaded to a pre-equilibrated column of Nickel agarose or Glutathione sepharose 4B. The column was then washed twice with 10× bed volume of chilled PBS. Then thrombin at the concentration of approx 1 U/100 µg of loaded protein (in 50 mM Tris-HCl, pH8.0) was applied on the column (if used glutathione-sepharose affinity chromatography) and incubated for 5 hours at 22-30° C. The recombinant enzyme was eluted with elution buffer (50 mM Tris-Cl, pH8.0) in 20-25 ml. The fractions with higher activity were pooled together. Purity of the eluted protein was checked on SDS PAGE. Concentration of the protein was determined by Bradford method using BSA as standard (24)

Subcloning in Expression vector: The forward (TR-ATG) and reverse (TR-TAA) primers were designed from LDdTR sequence that contain Nco1 and BamH1 restriction sites (bold and underlined) respectively to facilitate cloning directionally into pET-41a expression vector (Novagen). The primer sequences were, TR-ATG primer: 5'GCATATCCATGGC-CCGCGCGTACGACCTCGTG (forward) (SEQ ID No. 3); TR-TAA primer: 5' CGCGCGGATCCTCAGAGGTTGCT-GCTGAGCTT (Reverse) (SEQ ID No. 4). Amplification was performed as described above using cloned LDdTR as template. The annealing was kept at 50° C. with final extension at 72° C. for 4 min. The purified coding region of *L. donovani* TR was digested with Nco1 and BamH1 to provide cohesive ends and ligated to pET41a (Novagen) treated with same enzymes and dephosphorylated. The resulting construct was first transformed into the DH5α competent cells and selected by kanamycin (50 µg/ml) resistance (figs describes the *Leishmania donovani* Trypanothione Reductase construct in pET 41a expression vector). After confirmation of the sequence of LddTRpET41a, the construct was transformed again into the BL21DE3 expression cells for heterologous expression of the protein. Clones were selected by kanamycin (50 µg/ml) resistance. Glycerol stock of clone LddTRpET41aDE3 was prepared in LB and stored at −80° C.

Enzyme activity of recombinant LdTR expressed in *E. coli*: Single clone of *E. coli* cells containing plasmid with the LdTR gene (LdTRpET41aDE3) was inoculated in 10 ml LB medium with kanamycin (50 µg/ml) at 250 C overnight. The overnight grown culture was then transferred to 100 ml LB in 1:100 ratio containing 50 µg/ml kanamycin and incubated further at 22° C. and 200 rpm. The culture was grown up to the (O.D.) 600=0.4-0.5 and induced with 1 mM IPTG (isopropyl-D-thiogalactopyranoside) and further incubated at 22° C. overnight at 200 rpm. *E. coli* BL21 (DE3) containing pET41a plasmid alone was grown in the same way. The cells were harvested by centrifugation at 6000 rpm for 20 min. The wet cell pellet was suspended into 20 ml of lysis buffer (10 mm K+Po4—buffer pH 7.2, 10 mM EDTA, 0.01% tritonX100, 0.1 mM PMSF) and sonicated with a power at 50 W (six times thirty sec. pulse with one minute interval). The cell homogenate was centrifuged at 12000 g for 20 min. After removing debris clear supernatant was tested for TR activity. Marked activity of TR was present in lysate of experimental cells while no activity was present in control cells. Glutathione reductase activity was almost same in control and experiment *E. coli* lysate. Protein concentration was determined by Bradford method using BSA as standard.

Example 3

Purification and Enzyme Assay of Recombinant LdTR

Single clone LddTRpET41aDE3 was inoculated in 10 ml LB medium with kanamycin (50 µg/ml) at 25° C. overnight. The overnight grown culture was then transferred to 100 ml LB in 1:100 ratio containing 50 µg/ml kanamycin and incubated further at 22° C. and 200 rpm. The culture was grown up to the (O.D.)$_{600}$=0.4-0.5 and induced with 1 mM IPTG (isopropyl-D-thiogalactopyranoside) and further incubated at 22° C. overnight at 200 rpm. The cells were harvested by centrifugation at 6000 rpm for 20 min. The wet cell pellet was either stored at −20° C. or suspended into 20 ml of lysis buffer (10 mM K$^+$Po$_4^-$ buffer pH 7.2, 10 mM EDTA, 0.01% tritonX100, 0.1 mM PMSF) and sonicated with a power at 50 W (six times thirty sec. pulse with one minute interval). The cell homogenate was centrifuged at 12000 g for 20 min. After removing debris clear supernatant (20 ml) was loaded to a pre-equilibrated resin (5× washed with 10 ml and re-suspended in 8 ml of 10 mM Potassium phosphate buffer pH 7.2), glutathione sepharose 4B column. The column was then washed twice with 10× bed volume (25 ml each time) of chilled PBS at flow rate 1 ml/min. Then thrombin (15 IU/5 ml of 50 mM Tris-Cl, pH 8.0) at the concentration of 1 U/100 µg protein of *E. coli* lysate was applied on the column and incubated for 5 hours at 22° C. The recombinant enzyme was eluted with five bed volumes of elution buffer (5×5 ml of 50 mM Tris-Cl, pH8.0). Final elution was performed with 5 ml of 10 mM glutathione. The fractions with higher activity (Fractions 1 & 2) were pooled together and purity was checked on SDS PAGE. The expressed LdTR showed a molecular mass of about 54.6 Kd in SDS-PAGE (FIG. 6 describes the SDS PAGE analysis of expressed and purified recombinant *Leishmania donovani* trypanothione reductase under reducing conditions on 10% gel. Lane 1 is Crude *E. coli* supernatant, Lane 2, Flow through; Lane 3, Washing of the column; Lane 4, BSA (marker); Lane 5-7 are 54.6 Kd purified LdTR fractions; Lane 8, LdTR and GST fractions). The molecular mass determined by MALDI_TOFF was 54.6 Kd and was in full agreement with the amino acids composition.

Example 4

Enzyme Assay, Kinetics and Inhibition Studies

Trypanothione reductase activity was routinely assayed spectrophotometrically at 340 nm, as previously described (25). The reaction mixture contained 20-100 mM HEPES pH 7.2-7.8, 20 µM-1 mM EDTA, 80-200 µM NADPH and 15-50 µM TS$_2$. One unit of enzyme activity is defined as that amount of enzyme required to convert 1 µmol of NADPH to NADP per minute at 25° C. Protein was assayed according to the method of Bradford (1976) as supplied by Bangalore Genei with Bovine serum albumin as a standard. For comparative kinetic studies, assay was performed at 50 µM NADPH and at 5-100 µM concentrations of TS$_2$ and at 50 µM TS$_2$ and at 10-200 µM concentrations of NADPH.

Effect of various leishmanicidal (Sodium stibogluconate (SAG), sodium antimony (SbIII), trypanosomaticidal (Nifurtimox (NX), Nitrofurazone (NF), melarson oxide (MO), melarsoprole (MP), known inhibitors of glutathione reductase (carmustine BCNU), 1 chloro, 2-4dinirobenzene (CDNB) and antileishmanial moiety of antimony (SbIII) was studied on recombinant protein at 10-100 µM concentrations.

Trypanothione reductase activity was routinely assayed spectrophotometrically at 340 nm, as previously described (25). The reaction mixture contained 100 mM HEPES pH 7.8, 20 µM EDTA, 80 µM NADPH and 50 µM TS$_2$. The reaction was allowed to proceed for 5 min. and change in O.D. was monitored every after 30 sec. One unit of enzyme activity is defined, as that amount of enzyme required to convert 1 µmol of NADPH to NADP per minute at 25° C. The purified recombinant enzyme has a specific activity of 12.5 U/mg. protein. Purification procedure leads to 20 fold purification from the soluble content of *E. coli* lysate. The total yield was 16 mg/lit (FIG. 7 describes the fold purification of Recombinant *Leishmania donovani* Trypanothione Reductase). The purified protein specifically catalyzed reduction of oxidized trypanothione reductase and did not catalyze reduction of oxidized glutathione (FIG. 8 describes the substrate specificity of recombinant purified *Leishmania donovani* Trypanothione Red). For comparative kinetic studies, assay was performed at 50 µM NADPH and varying concentration of TS$_2$ (20, 40, 60, 80 & 100) and at 50 µM TS$_2$ and varying concentration of NADPH (20, 40, 60, 80, 100 & 150). The Vmax was found to be 200 µM/ml/min, 125 µM/ml/min and the Km value were 50 µM & 20 µM respectively and in agreement to purified enzyme from the parasite (19,27) (FIG. 9 which describes the kinetics of Trypanothione Reductase with NADPH and trypanothione).

Effect of Leishmanicidal compounds (Sodium stibogluconate, Antimony potassium tartrate), trypanosomicidal compounds (Melarson oxide, Melarsoprol, Nifurtimox, Nitrofuran), glutathione metabolism inhibitors (BSO, BCNU and CDNB) was studied on the activity of recombinant LDdTR at 50 and 100 µM concentration. SbIII the trivalent antimonial, active form of the antimony is having profound effect on TR activity in comparison to SAG, the pentavalent form of the antimony. Among trypanosomaticidal compounds Melarsen Oxide inhibited TR more than 95% at 50 uM concentration. This compound forms an adduct with trypanothione thus inhibits the enzyme maximally. The other compound namely Nifurtimox, Nitrofurazone and Melarsoprol, the known subversive substrate for TR also inhibited the Leishmanial TR to 20-60%, which is in accordance with the previous reports (26), The Glutathione metabolism inhibitors did not show much effect on TR activity (FIG. 10 describes the effect of inhibitors on Leishmanial TR activity).

Thus we can infer that the described invention provide a simple and most efficient method for the heterologous expression of Leishmanial proteins in prokaryotic system Advantages The main advantages of present invention are:

The present invention is aimed for the large-scale production of leishmanial protein trypanothione reductase in its native form in *E. coli*, which is otherwise present in very small quantity in *Leishmania* parasite.

The lengthy and difficult procedure for purification of the enzyme from *Leishmania* parasite is replaced with very simple and single step purification from bacterial cells.

The expressed recombinant enzyme specifically reduces oxidized trypanothione and is present in soluble fraction of the total lysate.

The enzyme is in soluble fraction and requires no further treatment for down stream applications.

Total yield of the purified fraction is much higher than the reported methods.

The purified active enzyme is stable at 4° C. for more than three months.

The protein/enzyme can be utilized for large scale screening of antileishmanials compounds in target based high throughput screening in drug development program.

Provided below is the sequence listing information SEQ ID Nos. 1, 2, 3, 4

SEQUENCE LISTING

GENERAL INFORMATION

APPLICANT: CSIR

TITLE OF THE INVENTION: Heterologus expression of Trypanothione Reductase from *Leishmania donovani* in a prokaryotic system

NUMBER OF SEQUENCES: 04

CORRESPONDENCE ADDRESS: Central Drug Research Institute, Chattar Manzil Palace, Lucknow-226001 (U.P.), India INFORMATION FOR SEQUENCE ID No:1

1. SEQUENCE CHARACTERISTICS:
    1. LENGTH: 1507 bp.
    2. TYPE: DNA

```
5'atgtcccgcgcgtacgacctcgtggtgcttggcgccggatctggaggt
ctggaggcgggatggaaccccggccgtcacgcacaaaaagaaggtcgggcc
gtcgtcgatgtgcaggcgacgcacggtccgccgctcttcgctcggcggca
cgtgcgtgaacgtcggctgcgtgccaaagaaactcatggtgacaggtgcc
cagtacatggacctgatccgtgagtctggcggcttcgatgggagatggac
cgcgaatcgctctgccccactggaagacgctcatcgccgcgaagaacaa
ggtggtgaacagcatctacgagagctacaagagcatgttcgctgatacgg
agggcctcagctttcacatgggcttcggtgccatcaatacgctcacccgg
tggtggtgcgcaagtcggaagacccacacagcgacgtgctgggaccctcg
```

-continued

```
acacggattacatcctcattgccaccggctcttggccgacgcgcctcgga
gtccccggcgacgagttctgcatcacgagcaacgaggcttctacctcgag
gatgcccccaagcggatgctgtgcgtcggcggctgctacatcgccgttga
gtttgccggcatcttcaacggctacaagcccaggggtggctatgtcgacc
tgtgctaccgcggcgatcttattttgcgcggcttcgatacagaggtgcgc
aagagcctgacgaagcagctgggggcgaacggaataagagtgcgtacaaa
cttgaacccgacgaagatcacgaagaatgaggacggctcgaatcacgttc
acttcaacgatggcacggaggaggactacgatcaggtcatgctcgcgatc
ggtcgcgtgccgcgctcgcaggcactacagctcgccaaggccggcgtccg
aacaggaaagaacggtgccgtgcaggtcgacgcgtattcgaagacatcgg
tggacaacatctacgccatcgccatcggcgacgtgacgaaccgcgtgatg
ttgacgccggtggccatcaacgaaggcgccgccttcgttgaaaccgtctt
cggtggcaagccccgcgccaccgaccacaggaaggtcgcgtgccgcgtgt
tctccataccgccgatcggcacgtgcggcatgacggaggaggaggcggcg
aagaactacgaaaccgtcgccgtgtacgcgagctctttcacgcccttat
gcacaacatcagcggcagcaagcacaaggaattcacgatccgcatcatca
cgaacgaatccaacggcgaggttctgggtgttcacatgctcggcgacagt
gcgcctgagatcatccagagcgtcggcatttgcatgcagatgggcgccaa
gatcagcggcttccacagcaccatcggagtccacccgacgagcgccgagg
agctctgctccatgcgcactccagcgtacttctacgagagtggcaagcgc
g tcgaaaagct cagcagcaac ctctgaagag ggaggagagatgaag
aagaacgcgtcaa3'
```

3. ORGANISM: *Leishmania donovani*
4. IMMEDIATE: Natural sequence
5. NAME/KEY: DNA sequence
6. SEQUENCE ID #1

INFORMATION FOR SEQUENCE ID No: 2

1. SEQUENCE CHARACTERISTICS:
    1. LENGTH: 491 bp.
    2. TYPE: Protein

```
MSRAYDLVVLGAGSGGLEAGWNPAVTHKKKVGPSSMCRRRTVRRSSLGGT
CVNVGCVPKKLMVTGAQYMDLIRESGGFGWEMDRESLCPHWKTLIAAKNK
VVNSIYESYKSMFADTEGLSFHMGFGAINTLTRWWCASRKTHTATCWDPR
HGLHPHCHRLLADAPRSPRRRVLHHEQRGFYLEDAPKRMLCVGGCYIAVE
FAGIFNGYKPQGGYVDLCYRGDLILRGFDTEVRKSLTKQLGANGIRVRTN
LNPTKITKNEDGSNHVHFNDGTEEDYDQVMLAIGRVPRSQALQLAKAGVR
TGKNGAVQVDAYSKTSVDNIYAIAIGDVTNRVMLTPVAINEGAAFVETVF
GGKPRATDHRKVACRVFSIPPIGTCGMTEEEAAKNYETVAVYASSFTPLM
HNISGSKHKEFTIRIITNESNGEVLGVHMLGDSAPEIIQSVGICMQMGAK
ISGFHSTIGVHPTSAEELCSMRTPAYFYESGKRVEKLSSNL
```

3. ORGANISM: *Leishmania donovani*
4. IMMEDIATE: Natural sequence
5. NAME/KEY: Amino acid sequence
6. SEQUENCE ID #2

INFORMATION FOR SEQUENCE ID No: 3

1. SEQUENCE CHARACTERISTICS:
   1. LENGTH: 32 bp.
   2. TYPE: DNA

5'GCATATCCATGGCCCGCGCGTACGACCTCGTG3'

3. ORGANISM: *Leishmania donovani*
4. IMMEDIATE: Artificial sequence
5. NAME/KEY: Oligonucleotide primer (forward)
6. SEQUENCE ID #3

INFORMATION FOR SEQUENCE ID No: 4

1. SEQUENCE CHARACTERISTICS:
   1. LENGTH: 32 bp.
   2. TYPE: DNA

5'CGCGCGGATCCTCAGAGGTTGCTGCTGAGCTT3'

3. ORGANISM: *Leishmania donovani*
4. IMMEDIATE: Artificial sequence.
5. NAME/KEY: Oligonucleotide primer (Reverse Primer)
6. SEQUENCE ID #4

REFERENCES

1. WHO report on Leishmaniasis, 1993
2. WHO report on Leishmaniasis, 1994
3. Berman, J. D. (1988) Chemotherapy for Leishmaniasis: Biochemical mechanisms clinical efficacy and future strategies; *Rev. Inf. Dis.;* 10; 560-586
4. Herwaldt, B. L. and Berman, J. D. (1992). Recommendations for treating leishmaniasis with sodium stibogluconate (pentostam) and review of pertinent clinical studies; *Am. J. Trop. Med. Hyg;* 46; 296-306
5. Peter, W. (1981), The treatment of kala-azar; New approach to an old problem, *Indian journal of medical research,* 73 (suppl.), 1-18
6. Thakur, C. P., Kumar, M., Singh, S. K. et al (1984), Comparison of regimes of treatment with sodium stibogluconate in India: a randomized study. *British medical journal;* 26, 21-25
7. WHO (1984) The Leishmaniasis: report of a WHO expert committee, WHO technical report series; 701, 99-108,
8. WHO (1990) The control of Leishmaniasis report of an expert committee WHO technical report series; 793, 50-55
9. Shyam Sundar (2001) Drug resistance in Indian visceral leishmaniasis, *Tropical medicine and international health;* 6 (11), 849-854
10. Villa H., Perez-Peatejoy, Garcia-Estradac, Reguera, R. M., Reguena, J. M., Tekwani, B. L., Balana-Fouce, R., Ordonez, D. (2003), Molecular and functional characterization of Adenylate kinase2 gene from *L. donovani, European J. Biochem.,* 270 (21) 4339-47
11. Perez-Pertejoy, Reguera, R. M., Villa, H., Garcia-Estrada, C., Balana-Fouce, R. Pajares, M. A. and Brdonez, D. (2003), *Leishmania donovani* Methionine adenosyltransferase—Role of cysteine residue in the recombinant enzyme, *European J. Biochem.,* 270 (1), 28-35
12. Rafati, S., Nakhaee, A., Taheri, T., Ghashghaii, A., Salmanian, A. H., Jimnez, M., Mohebali, M., Masina, S. and Fasel, N. (2003) Expression of Cysteine Proteinase type 1 and II of *Leishmania infantum* and their recognition by sera during canine and visceral leishmaniasis, *Exp. Parasitol;* 103 (3-4), 143-151
13. Larreta, R., Soto, M., Alones, C. and Requena, R. M. (2000), *Leishmania infantum:* Gene cloning of the GRP 94 homologue, its expression as recombinant protein and analysis of antigenicity, *Exp. Parasitol.,* 96 (2), 108-115
14. Helen P Price, Malini R. Mehon, Chrysoula Panethymitaki, David Goulding, Paul G. Mekean and Deberoh F. Smith (2003), *J. Bio. Chem.,* 278 (9), 7200-7214
15. Javier Vernal, Juan Jose Cazzulo and Cristina Nowicki (2003), Cloning and heterologous expression of broad specificity aminotransferase of *Leishmania* promastigotes, *FEMS microbiology Letters* 229, 217-222
16. Abdel Razek-Desouky, Charles A. Specht, Lynn Soong and Joseph M. Vinetz (2001), *Leishmania donovani* expression and characterization of *E. coli.* expressed recombinant Chitinase Ld CHT1, *Exp. Parasitol.* 99 (3-4), 220-225
17. Francis X. Sullivan, Spencer L. Shames and Christopher T. Walsh (1989), Expression of *Trypanosoma congolens* Trypanothione reductase in *E. coli.* Over production, purification and characterization, *Biochemistry,* 28, 4986-4992
18. Shames, S. L., Fairlamb, A. H., Cerami, A. and Walsh, C. T. (1986). Purification and characterization of trypanothione reductase from *Crithidia fasciculata;* a newly discovered member of family of disulphide containing flavoprotein reductases; Biochemistry; 25; 3519-3526
19. Shames, S. L., Fairlamb, A. H., Cerami, A. and Walsh, C. T. (1986). Purification and characterization of trypanothione reductase from *Crithidia fasciculata;* a newly discovered member of family of disulphide containing flavoprotein reductases; Biochemistry; 25; 3519-3526
20. R. Luise KRAUTH-Siegel, Burkhard Enders, Graemeb HENDERSON, A. H. FAIRLAMB and R. Heiner SCHIRNER (1987), Trypanothione reductase from *Trypanosoma Cruzi, European J Biochem.* 164, 123-128
21. Francis X. Sullivan and Christopher T. Walsh (1991) Cloning, sequencing, overproduction and purification of trypanothione reductase from *T. cruzi, Mol. Biochem. Parasitol.,* 44, 1991, 145-148
22. Taylor, M. C., Kelly, J. M., Chapman, C. J., Fairlamb, A. H. and Miles, M. A. (1994). The structure, organization, and expression of the *Leishmania donovani* gene encoding trypanothione reductase. *Mol. Biochem. Parasitol.;* 64; 293-301
23. Cunnigham, M. L. and Fairlamb, A. H> (1995) Trypanothione reductase from *L. donovani:* purification, characterization and inhibition by trivalent antimonials, *Eur. J Biochem,* 230; 462-468
24. M. M. Bradford (1989), A rapid and sensitive method for the quantitation of microgram quantities of proteins utilizing the principle of protein dye binding, *Anal. Biochem.* 177, 248-254
25. Cunningham, M. L., Zvelebil, M. J. J. M. & Fairlamb, A. H. (1994) Mechanism of inhibition of trypanothione reductase and glutathione reductase by trivalent organic arsenials, Eur. J. Biochem. 221, 285-295
26. Lemma, A. and Schilter, E. L. (1964). Extracellular cultivation of the Leishmanial bodies of species belonging to the protozoan genus *Leishmania; Exp. Parasitol.;* 15; 503-513
27. Borges, A., Cunnigham, M. L., Tovar, J. and Fairlamb, A. H. (1995), Site directed mutagenesis of the redox active cysteines of *Trypanosoma cruzi* trypanothione reductase, *European J. Biochem.* 228, 745-752

We claim:

1. A process for heterologus expression of functionally active enzyme trypanothione reductase of *Leishmania donovani* strain Dd8 (WHO Reference No. MHOM/IN/80/Dd8; available in ATCC, No. 50212) in a prokaryotic system, said process comprising the steps of:
   (a) amplifying, identifying and isolating the Open Reading Frame (ORF) of trypanothione reductase having the nucleotide sequence of SEQ ID NO: 1 and the corresponding protein of SEQ ID NO: 2 using forward primer consisting of SEQ ID NO: 5 and reverse primer consisting of SEQ ID NO: 6, (b) cloning of the amplified product of SEQ ID NO: 1 of step (a) in commercial TA cloning vector, (c) transforming and propagating the clone of step (b) in *E. coli* cells, (d) purifying plasmid DNA of step (c) and using it as a template for amplification of LddTR ORF having Nco1 and Bam H1 flanking restriction sites for directional cloning in an expression vector, (e) subcloning of LddTR-ORF in commercial pET41 expression vector, (f) transforming the cloned LddTR-ORF of step (e) in *E. coli* cells and studying the expression of LddTR protein in bacterial lysate under different conditions of expression and selection of conditions for maximum expression, (g) purifying the LddTR protein of SEQ ID NO: 2 from step (f) to homogeneity, and (h) analyzing biochemical parameters (substrate specificity, specific activity, Kin, Vmax, and effect of inhibitors) of the expressed trypanothione reductase enzyme (LddTR) to establish the heterologous expression of trypanothione reductase of *Leishmania donovani* of SEQ ID NO: 2 in a prokaryotic system.

2. A process as claimed in claim 1, wherein the enzyme trypanothione reductase having the nucleotide sequence of SEQ ID NO: 1 and corresponding protein of SEQ ID NO: 2 is central to thiol metabolism of the parasite and essential for the survival of the parasite in the macrophage system.

3. A process as claimed in claim 1, wherein the enzyme trypanothione reductase is a drug target for prevention and treatment of *Leishmania donovani.*

4. A process as claimed in claim 1, wherein the amplification conditions in step (a) are single cycle at 95° C. for 9 min followed by 25 cycles of 95° C. for 1-2 min., 45° C.-47° C. for 1 min. and 72° C. for 2-3 min and final single cycle of 72° C. for 4 min.

5. A process as claimed in claim 1, wherein the complete ORF of trypanothione reductase of *Leishmania donovani* strain Dd8 (WHO Reference No. MHOM/IN/80/Dd8; available in ATCC NO. 50212) of SEQ ID NO: 1, in step (a) was amplified using forward primer having the nucleotide sequence of SEQ ID NO: 3 and reverse primer having the nucleotide sequence of SEQ ID NO: 4.

6. A process as claimed in claim 1, wherein cloning vectors in step (b) is selected from group comprising of pCRTOPOII, TA and pGLM-T.

7. A process as claimed in claim 6, wherein cloning vector selected is pGLM-T.

8. A process as claimed in claim 1, wherein cloning conditions in step (b) are:

(a) Vector and insert ratio 1:3 (1.5 μl:4.5 μl; 120 ng of insert DNA), (b) T4 DNA ligase 1 μl (10 U/μl), (c) 10× phosphate buffer, and (d) Ligation conditions 14° C. for 18 hrs.

9. A process as claimed in claim 1, wherein expression vectors in step (c) is selected from group comprising of pQE 30, pET 21d, pET 28b, pET 41a and pGEX4T vectors.

10. A process as claimed in claim 9, wherein expression vector selected is pET41a.

11. A process as claimed in claim 1, wherein the prokaryotic cloning system in step (f) is selected from group comprising of JM 109 *E. coli* cells.

12. A process as claimed in claim 1, wherein the prokaryotic expression system in step (f) is selected from group comprising of BL21 DE3, M-15, or BL21DE3 pLys *E. coli* cells.

13. A process as claimed in claim 12, wherein the expression prokaryotic system selected is BL21 DE3 *E. coli* cells.

14. A process as claimed in claim 1, wherein the purification steps in step (g) further comprises:
 (a) growing the *E. coli* cells containing LdTRORF overnight,
 (b) harvesting cells of step (a) and suspending them in lysis buffer,
 (c) sonicating the harvested cells and removing the debris from the harvested cells of step (b),
 (d) resuspending the cells again in phosphate buffer,
 (e) loading the suspended cells of step (d) in pre-equilibrated column of glutathione sepharose 4B column and incubating for about 5 hrs. at 22-20 mm,
 (f) washing the column during incubation in step (e) twice with chilled PBS buffer, and adding thrombin at concentration of 1 U/100 μg of loaded protein, and
 (g) eluting the recombinant enzyme from step (f) by adding 20-25 ml of elution buffer.

15. A process as claimed in claim 14 wherein the *E. coli* cells in step (a) are grown at temperature of about 22-27° C.

16. A process as claimed in claim 14 wherein the lysis buffer in step (b) comprises of potassium phosphate buffer (10 mM) pH 7.2, 10 mM EDTA, 0.01% triton X 100, 0.1 mM PMSF.

17. A process as claimed in claim 14 wherein sonication in step (c) is done 3-5 times for 30 sec to 1 min pulse with 1-2 min. cooling interval.

18. A process as claimed in claim 14 wherein the debris in step (c) is removed by centrifugation at 9000-120000 g for 15-20 min.

19. A process as claimed in claim 14 wherein the elution buffer in step (g) is 50 mM Tris-HCl, pH 8.0.

20. A process as claimed in claim 14 wherein the purified recombinant trypanothione reductase (LddTR) isolated is having molecular mass of 54.6 kd.

21. A process as claimed in claim 14 wherein purified recombinant trypanothione reductase (LddTR) is having specific activity of 12.5 U/mg.

22. A process as claimed in claim 14 wherein the total yield of purified recombinant trypanothione reductase (LddTR) is 16 mg/liter.

23. A process as claimed in claim 14 wherein $V_{max}$ of purified recombinant trypanothione reductase (LddTR) with $TS_2$ is 200 μM/ml/min and with NADPH is 125 μM/ml/min.

24. A process as claimed in claim 14 wherein $K_m$ of purified recombinant trypanothione reductase (LddTR) with $TS_2$ is 50 μM and with NADPH is 20 μM.

25. Isolated oligonucleotide primers having SEQ ID NO: 3 (forward primer) or SEQ ID NO: 4 (reverse primer) for isolating Open Reading Frame (ORF) of trypanothione reductase having the nucleotide sequence of SEQ ID NO: 1 and corresponding protein of SEQ ID NO: 2, from *Leishmania donovani* genomic DNA by polymerase chain reaction.

26. A process as claimed in claim 1, wherein the amplification conditions in step (d) are:
 (a) a single cycle at 95° C. for 9 min. followed by
 (b) 25 cycles of 95° C. for 1-2 min., 50° C. for 1 min., and 72° C. for 2 min., followed by
 (c) a single cycle of 72° C. for 4 min.

27. A process as claimed in claim 1, wherein the amplification in step (d) uses DNA generated in step (b), wherein the forward primer has the nucleotide sequence of SEQ ID NO: 3 and the reverse primer has the nucleotide sequence of SEQ ID NO: 4.

28. A process as claimed in claim 1, wherein the amplified product in step (d) is
 (a) digested with Nco1 and Bam H1 and
 (b) purified on agarose gel.

29. A process as in claim 1, wherein the *E. coli* selected in steps (c) and (d) is DH5α.

30. A process as claimed in claim 14, wherein the *E. coli* cells in step (a) are diluted 1:100 times in fresh medium with kanamycin (50 μg/ml) and allowed to grow at 21-23° C., 200 rpm until the OD reaches 0.4-0.5.

31. A process as claimed in claim 14 wherein cells in step (b) are induced with 1 mM IPTG and further incubated 16-18 hours at 22° C., 200 rpm.

32. A process as claimed in claim 1, wherein the purification in step (g) further comprises:
 (a) growing BL21 DE3 *E. coli* cells containing LddTR construct in pET41a expression vector overnight in 10 ml LB with kanamycin (50 μg/ml) at 25° C.,
 (b) diluting the overnight culture from step (a) to a concentration of 1:100 in fresh medium with kanamycin (50 μg/ml) and growing the diluted culture at 22° C., 200 rpm until the OD reaches 0.45,
 (c) inducing the culture of step (b) with IPTG and allowing the culture to grow overnight at 22° C., 200 rpm,
 (d) harvesting the cells of step (c) and suspending the cells in lysis buffer,
 (e) sonicating the cell suspension and removing the cellular debris to get clear cell lysate,
 (f) loading the cell lysate of step (e) in a pre-equilibrated gluthathione-sepharose 4B column,
 (g) washing the column from step (f) twice with chilled PBS buffer, adding thrombin at a concentration of 1 U/100 mg of loaded protein, and incubating for 5 hours, and
 (h) eluting the trypanothione reductase from step (g) by adding 20-25 ml of elution buffer.

\* \* \* \* \*

UNITED STATES PATENT AND TRADEMARK OFFICE
CERTIFICATE OF CORRECTION

| | | |
|---|---|---|
| PATENT NO. | : 7,785,850 B2 | Page 1 of 1 |
| APPLICATION NO. | : 10/996174 | |
| DATED | : August 31, 2010 | |
| INVENTOR(S) | : Goyal et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 714 days.

Signed and Sealed this
Eleventh Day of January, 2011

David J. Kappos
*Director of the United States Patent and Trademark Office*

SEQUENCE LISTING

<160> NUMBER OF SEQ ID NOS: 12

<210> SEQ ID NO 1
<211> LENGTH: 1507
<212> TYPE: DNA
<213> ORGANISM: Leishmania donovani

<400> SEQUENCE: 1

```
atgtcccgcg cgtacgacct cgtggtgctt ggcgccggat ctggaggtct ggaggcggga      60
tggaacccgg ccgtcacgca caaaaagaag gtcgggccgt cgtcgatgtg caggcgacgc     120
acggtccgcc gctcttcgct cggcggcacg tgcgtgaacg tcggctgcgt gccaaagaaa     180
ctcatggtga caggtgccca gtacatggac ctgatccgtg agtctggcgg cttcgatggg     240
agatggaccg cgaatcgctc tgcccccact ggaagacgct catcgccgcg aagaacaagg     300
tggtgaacag catctacgag agctacaaga gcatgttcgc tgatacggag ggcctcagct     360
ttcacatggg cttcggtgcc atcaatacgc tcacccggtg gtggtgcgca gtcggaaga      420
cccacacagc gacgtgctgg gaccctcgac acggattaca tcctcattgc caccggctct     480
tggccgacgc gcctcggagt ccccggcgac gagttctgca tcacgagcaa cgaggcttct     540
acctcgagga tgcccccaag cggatgctgt gcgtcggcgg ctgctacatc gccgttgagt     600
ttgccggcat cttcaacggc tacaagcccc agggtggcta tgtcgacctg tgctaccgcg     660
gcgatcttat tttgcgcggc ttcgatacag aggtgcgcaa gagcctgacg aagcagctgg     720
gggcgaacgg aataagagtg cgtacaaact tgaacccgac gaagatcacg aagaatgagg     780
acggctcgaa tcacgttcac ttcaacgatg gcacggagga ggactacgat caggtcatgc     840
tcgcgatcgg tcgcgtgccg cgctcgcagg cactacagct cgccaaggcc ggcgtccgaa     900
caggaaagaa cggtgccgtg caggtcgacg cgtattcgaa gacatcggtg gacaacatct     960
acgccatcgc catcggcgac gtgacgaacc gcgtgatgtt gacgccggtg gccatcaacg    1020
aaggcgccgc cttcgttgaa accgtcttcg gtggcaagcc ccgcgccacc gaccacagga    1080
aggtcgcgtg ccgcgtgttc tccataccgc cgatcggcac gtgcggcatg acggaggagg    1140
aggcggcgaa gaactacgaa accgtcgccg tgtacgcgag ctctttcacg cccttatgc     1200
acaacatcag cggcagcaag cacaaggaat tcacgatccg catcatcacg aacgaatcca    1260
acggcgaggt tctgggtgtt cacatgctcg gcgacagtgc gcctgagatc atccagagcg    1320
tcggcatttg catgcagatg ggcgccaaga tcagcggctt ccacagcacc atcggagtcc    1380
acccgacgag cgccgaggag ctctgctcca tgcgcactcc agcgtacttc tacgagagtg    1440
gcaagcgcgt cgaaaagctc agcagcaacc tctgaagagg gaggagagat gaagaagaac    1500
gcgtcaa                                                              1507
```

<210> SEQ ID NO 2
<211> LENGTH: 491
<212> TYPE: PRT
<213> ORGANISM: Leishmania donovani

<400> SEQUENCE: 2

```
Met Ser Arg Ala Tyr Asp Leu Val Val Leu Gly Ala Gly Ser Gly Gly
 1               5                  10                  15

Leu Glu Ala Gly Trp Asn Pro Ala Val Thr His Lys Lys Val Gly
                20                  25                  30

Pro Ser Ser Met Cys Arg Arg Arg Thr Val Arg Arg Ser Ser Leu Gly
```

```
            35                  40                  45
Gly Thr Cys Val Asn Val Gly Cys Val Pro Lys Lys Leu Met Val Thr
 50                  55                  60
Gly Ala Gln Tyr Met Asp Leu Ile Arg Glu Ser Gly Gly Phe Gly Trp
 65                  70                  75                  80
Glu Met Asp Arg Glu Ser Leu Cys Pro His Trp Lys Thr Leu Ile Ala
                     85                  90                  95
Ala Lys Asn Lys Val Val Asn Ser Ile Tyr Glu Ser Tyr Lys Ser Met
                100                 105                 110
Phe Ala Asp Thr Glu Gly Leu Ser Phe His Met Gly Phe Gly Ala Ile
                115                 120                 125
Asn Thr Leu Thr Arg Trp Trp Cys Ala Ser Arg Lys Thr His Thr Ala
                130                 135                 140
Thr Cys Trp Asp Pro Arg His Gly Leu His Pro His Cys His Arg Leu
145                 150                 155                 160
Leu Ala Asp Ala Pro Arg Ser Pro Arg Arg Val Leu His His Glu
                165                 170                 175
Gln Arg Gly Phe Tyr Leu Glu Asp Ala Pro Lys Arg Met Leu Cys Val
                180                 185                 190
Gly Gly Cys Tyr Ile Ala Val Glu Phe Ala Gly Ile Phe Asn Gly Tyr
                195                 200                 205
Lys Pro Gln Gly Gly Tyr Val Asp Leu Cys Tyr Arg Gly Asp Leu Ile
                210                 215                 220
Leu Arg Gly Phe Asp Thr Glu Val Arg Lys Ser Leu Thr Lys Gln Leu
225                 230                 235                 240
Gly Ala Asn Gly Ile Arg Val Arg Thr Asn Leu Asn Pro Thr Lys Ile
                245                 250                 255
Thr Lys Asn Glu Asp Gly Ser Asn His Val His Phe Asn Asp Gly Thr
                260                 265                 270
Glu Glu Asp Tyr Asp Gln Val Met Leu Ala Ile Gly Arg Val Pro Arg
                275                 280                 285
Ser Gln Ala Leu Gln Leu Ala Lys Ala Gly Val Arg Thr Gly Lys Asn
                290                 295                 300
Gly Ala Val Gln Val Asp Ala Tyr Ser Lys Thr Ser Val Asp Asn Ile
305                 310                 315                 320
Tyr Ala Ile Ala Ile Gly Asp Val Thr Asn Arg Val Met Leu Thr Pro
                325                 330                 335
Val Ala Ile Asn Glu Gly Ala Ala Phe Val Glu Thr Val Phe Gly Gly
                340                 345                 350
Lys Pro Arg Ala Thr Asp His Arg Lys Val Ala Cys Arg Val Phe Ser
                355                 360                 365
Ile Pro Pro Ile Gly Thr Cys Gly Met Thr Glu Glu Ala Ala Lys
370                 375                 380
Asn Tyr Glu Thr Val Ala Val Tyr Ala Ser Ser Phe Thr Pro Leu Met
385                 390                 395                 400
His Asn Ile Ser Gly Ser Lys His Lys Glu Phe Thr Ile Arg Ile Ile
                405                 410                 415
Thr Asn Glu Ser Asn Gly Glu Val Leu Gly Val His Met Leu Gly Asp
                420                 425                 430
Ser Ala Pro Glu Ile Ile Gln Ser Val Gly Ile Cys Met Gln Met Gly
            435                 440                 445
Ala Lys Ile Ser Gly Phe His Ser Thr Ile Gly Val His Pro Thr Ser
            450                 455                 460
```

```
Ala Glu Glu Leu Cys Ser Met Arg Thr Pro Ala Tyr Phe Tyr Glu Ser
465                 470                 475                 480

Gly Lys Arg Val Glu Lys Leu Ser Ser Asn Leu
            485                 490

<210> SEQ ID NO 3
<211> LENGTH: 32
<212> TYPE: DNA
<213> ORGANISM: Artificial
<220> FEATURE:
<223> OTHER INFORMATION: Synthetic; TR-ATG forward primer

<400> SEQUENCE: 3
gcatatccat ggcccgcgcg tacgacctcg tg                              32

<210> SEQ ID NO 4
<211> LENGTH: 32
<212> TYPE: DNA
<213> ORGANISM: Artificial
<220> FEATURE:
<223> OTHER INFORMATION: Synthetic; TR-TAA reverse primer

<400> SEQUENCE: 4
cgcgcggatc ctcagaggtt gctgctgagc tt                              32

<210> SEQ ID NO 5
<211> LENGTH: 17
<212> TYPE: DNA
<213> ORGANISM: Artificial
<220> FEATURE:
<223> OTHER INFORMATION: Synthetic; L donovani Trypanothione Reductase
      forward primer

<400> SEQUENCE: 5
ctcgcgaaaa ttcttcg                                               17

<210> SEQ ID NO 6
<211> LENGTH: 22
<212> TYPE: DNA
<213> ORGANISM: Artificial
<220> FEATURE:
<223> OTHER INFORMATION: Synthetic; L. donovani Trypanothione Reductase
      reverse primer

<400> SEQUENCE: 6
gagatgaaga agaagggcct aa                                         22

<210> SEQ ID NO 7
<211> LENGTH: 491
<212> TYPE: PRT
<213> ORGANISM: Leishmania donovani

<400> SEQUENCE: 7

Met Ser Arg Ala Tyr Asp Leu Val Val Leu Gly Ala Gly Ser Gly Gly
1               5                   10                  15

Leu Glu Ala Gly Trp Asn Ala Ala Val Thr His Lys Lys Lys Val Ala
            20                  25                  30

Val Val Asp Val Gln Ala Thr His Gly Pro Pro Ala Leu Val Ala Leu
        35                  40                  45

Gly Gly Thr Cys Val Asn Val Gly Cys Val Pro Lys Lys Leu Met Val
    50                  55                  60

Thr Gly Ala Gln Tyr Met Asp Leu Ile Arg Glu Ser Gly Gly Phe Gly
65                  70                  75                  80
```

```
Trp Glu Met Asp Arg Glu Ser Leu Cys Pro Asn Trp Lys Thr Leu Ile
                85                  90                  95

Ala Ala Lys Asn Lys Val Val Asn Ser Ile Asn Glu Ser Tyr Lys Ser
            100                 105                 110

Met Phe Ala Asp Thr Glu Gly Leu Ser Phe His Met Gly Phe Gly Ala
        115                 120                 125

Leu Gln Asp Ala His Thr Val Val Arg Lys Ser Glu Asp Pro His
    130                 135                 140

Ser Asp Val Leu Glu Thr Leu Asp Thr Glu Tyr Ile Leu Ile Ala Thr
145                 150                 155                 160

Gly Ser Trp Pro Thr Arg Leu Gly Val Pro Gly Asp Glu Phe Cys Ile
                165                 170                 175

Thr Ser Asn Glu Ala Phe Tyr Leu Glu Asp Ala Pro Lys Arg Met Leu
            180                 185                 190

Cys Val Gly Gly Gly Tyr Ile Ala Val Glu Phe Ala Gly Ile Phe Asn
        195                 200                 205

Gly Tyr Lys Pro Cys Gly Gly Tyr Val Asp Leu Cys Tyr Arg Gly Asp
    210                 215                 220

Leu Ile Leu Arg Gly Phe Asp Thr Glu Val Arg Lys Ser Leu Thr Lys
225                 230                 235                 240

Gln Leu Gly Ala Asn Gly Ile Arg Val Arg Thr Asn Leu Asn Pro Thr
                245                 250                 255

Lys Ile Thr Lys Asn Glu Asp Gly Ser Asn His Val His Phe Asn Asp
            260                 265                 270

Gly Thr Glu Glu Asp Tyr Asp Gln Val Met Leu Ala Ile Gly Val Pro
        275                 280                 285

Arg Ser Gln Ala Leu Gln Leu Asp Lys Ala Gly Val Arg Thr Gly Lys
    290                 295                 300

Asn Gly Ala Val Gln Val Asp Ala Tyr Ser Lys Thr Ser Val Asp Asn
305                 310                 315                 320

Ile Tyr Ala Ile Gly Asp Val Thr Asn Arg Val Met Leu Thr Pro Val
                325                 330                 335

Ala Ile Asn Glu Gly Ala Cys Val Leu Leu Glu Thr Val Phe Gly Gly
            340                 345                 350

Lys Pro Arg Ala Thr Asp His Thr Lys Val Ala Cys Ala Val Phe Ser
        355                 360                 365

Ile Pro Pro Ile Gly Thr Cys Gly Met Thr Glu Glu Ala Ala Lys
    370                 375                 380

Asn Tyr Glu Thr Val Ala Val Tyr Ala Ser Ser Phe Thr Pro Leu Met
385                 390                 395                 400

His Asn Ile Ser Gly Ser Lys His Lys Glu Phe Met Ile Arg Ile Ile
                405                 410                 415

Thr Asn Glu Ser Asn Gly Glu Val Leu Gly Val His Met Leu Gly Asp
            420                 425                 430

Ser Ala Pro Glu Ile Ile Gln Ser Val Gly Ile Cys Met Lys Met Gly
        435                 440                 445

Ala Lys Ile Ser Asp Phe His Ser Thr Ile Gly Val His Pro Thr Ser
    450                 455                 460

Ala Glu Glu Leu Cys Ser Met Arg Thr Pro Ala Tyr Phe Tyr Glu Ser
465                 470                 475                 480

Gly Lys Arg Val Glu Lys Leu Ser Ser Asn Leu
                485                 490
```

<210> SEQ ID NO 8
<211> LENGTH: 491
<212> TYPE: PRT
<213> ORGANISM: Leishmania major

<400> SEQUENCE: 8

```
Met Ser Arg Ala Tyr Asp Leu Val Val Leu Gly Ala Gly Ser Gly Gly
1               5                   10                  15

Leu Glu Ala Gly Trp Asn Ala Ala Thr Tyr Lys Lys Lys Val Ala
            20                  25                  30

Val Val Asp Val Gln Ala Thr His Gly Pro Pro Phe Phe Ala Ala Leu
        35                  40                  45

Gly Gly Thr Cys Val Asn Val Gly Cys Val Pro Lys Lys Leu Met Val
    50                  55                  60

Thr Gly Ala Gln Tyr Met Asp Leu Ile Arg Glu Ser Gly Gly Phe Gly
65                  70                  75                  80

Trp Glu Met Asn Arg Glu Ser Leu Cys Pro Asn Trp Lys Thr Leu Ile
                85                  90                  95

Ala Ala Lys Asn Lys Val Val Asn Gly Ile Asn Glu Ser Tyr Lys Ser
            100                 105                 110

Met Phe Ala Asp Thr Glu Gly Leu Ser Phe His Met Gly Phe Gly Ala
        115                 120                 125

Leu Gln Asp Ala His Thr Val Leu Val Arg Lys Ser Glu Asp Pro Asn
    130                 135                 140

Ser Asp Val Leu Glu Thr Leu Asp Thr Glu Tyr Ile Leu Ile Ala Thr
145                 150                 155                 160

Gly Ser Trp Pro Thr Arg Leu Gly Val Pro Gly Asp Glu Phe Cys Ile
                165                 170                 175

Thr Ser Asn Glu Ala Phe Tyr Leu Glu Asp Ala Pro Lys Arg Met Leu
            180                 185                 190

Cys Val Gly Gly Gly Tyr Ile Ala Val Glu Phe Ala Gly Ile Phe Asn
        195                 200                 205

Gly Tyr Lys Pro Arg Gly Gly Tyr Val Asp Leu Cys Tyr Arg Gly Asp
    210                 215                 220

Leu Ile Leu Arg Gly Phe Asp Thr Glu Val Arg Lys Ser Leu Thr Lys
225                 230                 235                 240

Gln Leu Gly Ala Asn Gly Ile Arg Val Arg Thr Asn Leu Asn Pro Thr
                245                 250                 255

Lys Ile Thr Lys Asn Glu Asp Gly Ser Asn His Val His Phe Asn Asp
            260                 265                 270

Gly Thr Glu Glu Asp Tyr Asp Gln Val Met Leu Ala Ile Gly Arg Val
        275                 280                 285

Pro Arg Ser Gln Thr Leu Gln Leu Asp Lys Ala Gly Val Gln Thr Ala
    290                 295                 300

Lys Asn Gly Ala Val Gln Val Asp Ala Tyr Ser Lys Thr Ser Val Asp
305                 310                 315                 320

Asn Ile Tyr Ala Ile Gly Asp Val Thr Asn Arg Val Met Leu Thr Pro
                325                 330                 335

Val Ala Ile Asn Glu Gly Ala Ala Phe Ala Glu Thr Val Phe Gly Gly
            340                 345                 350

Lys Pro Arg Ala Thr Asp His Thr Lys Val Ala Cys Ala Val Phe Ser
        355                 360                 365

Ile Pro Pro Ile Gly Thr Cys Gly Met Thr Glu Glu Glu Ala Ala Lys
    370                 375                 380
```

```
Asn His Glu Thr Val Ala Val Tyr Glu Ser Cys Phe Thr Pro Leu Met
385                 390                 395                 400

His Asn Ile Ser Gly Ser Lys His Lys Glu Phe Met Ile Arg Ile Ile
            405                 410                 415

Thr Asp Gln Pro Ser Gly Glu Val Leu Gly Val His Met Leu Gly Asp
                420                 425                 430

Ser Ala Pro Glu Ile Ile Gln Ser Val Gly Ile Cys Met Lys Met Gly
            435                 440                 445

Ala Lys Ile Ser Asp Phe His Asn Thr Ile Gly Val His Pro Thr Ser
450                 455                 460

Ala Glu Glu Leu Cys Ser Met Arg Thr Pro Ala Tyr Phe Tyr Glu Asn
465                 470                 475                 480

Gly Lys Arg Val Glu Lys Leu Ser Ser Asn Leu
                485                 490
```

<210> SEQ ID NO 9
<211> LENGTH: 488
<212> TYPE: PRT
<213> ORGANISM: C. fasiculata

<400> SEQUENCE: 9

```
Met Ser Arg Ala Tyr Asp Leu Val Val Ile Gly Ala Gly Ser Gly Gly
1               5                   10                  15

Leu Glu Ala Gly Trp Asn Ala Ala Ser Leu His Lys Lys Arg Val Ala
                20                  25                  30

Val Ile Asp Leu Gln Lys His His Gly Pro Pro His Tyr Ala Leu Gly
            35                  40                  45

Gly Thr Cys Val Asn Val Gly Cys Val Pro Lys Lys Leu Met Val Thr
        50                  55                  60

Gly Ala Asn Tyr Met Asp Thr Ile Arg Glu Ser Ala Gly Phe Gly Trp
65                  70                  75                  80

Glu Leu Asp Arg Glu Ser Val Arg Pro Asn Trp Lys Ala Leu Ile Ala
                85                  90                  95

Ala Lys Asn Lys Ala Val Ser Gly Ile Asn Asp Ser Tyr Glu Gly Met
                100                 105                 110

Phe Ala Asp Thr Glu Gly Leu Thr Phe His Gln Gly Phe Gly Ala Leu
            115                 120                 125

Gln Asp Asn His Thr Val Leu Val Arg Glu Ser Ala Asp Pro Asn Ser
        130                 135                 140

Ala Val Leu Glu Thr Leu Asp Thr Glu Tyr Ile Leu Leu Ala Thr Gly
145                 150                 155                 160

Ser Trp Pro Gln His Leu Gly Ile Glu Gly Asp Asp Leu Cys Ile Thr
                165                 170                 175

Ser Asn Glu Ala Phe Tyr Leu Asp Glu Ala Pro Lys Arg Ala Leu Cys
                180                 185                 190

Val Gly Gly Gly Tyr Ile Ser Ile Glu Phe Ala Gly Ile Phe Asn Ala
            195                 200                 205

Tyr Lys Ala Arg Gly Gly Gln Val Asp Leu Ala Tyr Arg Gly Asp Met
        210                 215                 220

Ile Leu Arg Gly Phe Asp Ser Glu Leu Arg Lys Gln Leu Thr Glu Gln
225                 230                 235                 240

Leu Arg Ala Asn Gly Ile Asn Val Arg Thr His Glu Asn Pro Ala Lys
                245                 250                 255

Val Thr Lys Asn Ala Asp Gly Thr Arg His Val Val Phe Glu Ser Gly
```

```
                    260                 265                 270
Ala Glu Asp Tyr Asp Val Val Met Leu Ala Ile Gly Arg Val Pro Arg
                275                 280                 285

Ser Gln Thr Leu Gln Leu Asp Lys Ala Gly Val Glu Val Ala Lys Asn
            290                 295                 300

Gly Ala Ile Lys Val Asp Ala Tyr Ser Lys Thr Asn Val Asp Asn Ile
305                 310                 315                 320

Tyr Ala Ile Gly Asp Val Thr Asp Arg Val Met Leu Thr Pro Val Ala
                325                 330                 335

Ile Asn Glu Gly Ala Ala Phe Val Asp Thr Val Phe Ala Asn Lys Pro
            340                 345                 350

Arg Ala Thr Asp His Thr Lys Val Ala Cys Ala Val Phe Ser Ile Pro
        355                 360                 365

Pro Met Gly Val Cys Gly Tyr Val Glu Glu Asp Ala Ala Lys Lys Tyr
    370                 375                 380

Asp Gln Val Ala Val Tyr Phe Ser Ser Glu Thr Pro Leu Met His Asn
385                 390                 395                 400

Ile Ser Gly Ser Thr Tyr Lys Lys Pro Met Val Arg Ile Val Thr Asn
                405                 410                 415

His Ala Asp Gly Glu Val Leu Gly Val His Met Leu Gly Asp Ser Ser
            420                 425                 430

Pro Glu Ile Ile Gln Ser Val Ala Ile Cys Leu Lys Met Gly Ala Lys
        435                 440                 445

Ile Ser Asp Phe Tyr Asn Thr Ile Gly Val His Pro Thr Ser Glu Glu
    450                 455                 460

Leu Cys Ser Met Arg Thr Pro Ala Tyr Phe Tyr Gln Lys Gly Lys Arg
465                 470                 475                 480

Val Glu Lys Ile Asp Ser Asn Leu
                485

<210> SEQ ID NO 10
<211> LENGTH: 492
<212> TYPE: PRT
<213> ORGANISM: Trypanosoma brucei

<400> SEQUENCE: 10

Met Ser Lys Ile Phe Asp Leu Val Val Ile Gly Ala Gly Ser Gly Gly
1               5                   10                  15

Leu Glu Ala Gly Trp Asn Ala Ala Thr Leu Tyr Lys Lys Arg Val Ala
            20                  25                  30

Val Ile Asp Val Gln Thr His His Gly Pro Pro His Tyr Ala Ala Leu
        35                  40                  45

Gly Gly Thr Cys Val Asn Val Gly Cys Val Pro Lys Lys Leu Met Val
    50                  55                  60

Thr Gly Ala Gln Tyr Met Asp His Leu Arg Glu Ser Ala Gly Phe Gly
65                  70                  75                  80

Trp Glu Phe Asp Gly Ser Ser Val Lys Ala Asn Trp Lys Lys Leu Ile
                85                  90                  95

Ala Ala Lys Asn Glu Ala Val Leu Asp Ile Asn Lys Ser Tyr Glu Gly
            100                 105                 110

Met Phe Asn Asp Thr Glu Gly Leu Asp Phe Phe Leu Gly Trp Gly Ser
        115                 120                 125

Leu Glu Ser Lys Asn Val Val Val Arg Glu Thr Ala Asp Pro Lys
    130                 135                 140
```

```
Ser Ala Val Lys Glu Arg Leu Gln Ala Asp His Ile Leu Leu Ala Thr
145                 150                 155                 160

Gly Ser Trp Pro Gln Met Pro Ala Ile Pro Gly Val Glu His Cys Ile
                165                 170                 175

Ser Ser Asn Glu Ala Phe Tyr Leu Pro Glu Pro Pro Arg Arg Val Leu
            180                 185                 190

Thr Val Gly Gly Gly Phe Ile Ser Val Glu Phe Ala Gly Ile Phe Asn
        195                 200                 205

Ala Tyr Lys Pro Pro Gly Gly Lys Val Thr Leu Cys Tyr Arg Asn Asn
    210                 215                 220

Leu Ile Leu Arg Gly Phe Asp Glu Thr Ile Arg Glu Glu Val Thr Lys
225                 230                 235                 240

Gln Leu Thr Ala Asn Gly Ile Glu Ile Met Thr Asn Glu Asn Pro Ala
                245                 250                 255

Lys Val Ser Leu Asn Thr Asp Gly Ser Lys His Val Thr Phe Glu Ser
            260                 265                 270

Gly Lys Thr Leu Asp Val Asp Val Met Met Ala Ile Gly Arg Ile
        275                 280                 285

Pro Arg Thr Asn Asp Leu Gln Leu Gly Asn Val Gly Val Lys Leu Thr
    290                 295                 300

Pro Lys Gly Gly Val Gln Val Asp Glu Phe Ser Arg Thr Asn Val Pro
305                 310                 315                 320

Asn Ile Tyr Ala Ile Gly Asp Ile Thr Asp Arg Leu Met Leu Thr Pro
                325                 330                 335

Val Ala Ile Asn Glu Gly Ala Ala Leu Val Asp Thr Val Phe Gly Asn
            340                 345                 350

Lys Pro Arg Lys Thr Asp His Thr Arg Val Ala Ser Ala Val Phe Ser
        355                 360                 365

Ile Pro Pro Ile Gly Thr Cys Gly Leu Ile Glu Glu Val Ala Ala Lys
    370                 375                 380

Glu Phe Glu Lys Val Ala Val Tyr Met Ser Ser Phe Thr Pro Leu Met
385                 390                 395                 400

His Asn Ile Ser Gly Ser Lys Tyr Lys Lys Phe Val Ala Lys Ile Val
                405                 410                 415

Thr Asn His Ser Asp Gly Thr Val Leu Gly Val His Leu Leu Gly Asp
            420                 425                 430

Gly Ala Pro Glu Ile Ile Gln Ala Val Gly Val Cys Leu Arg Leu Asn
        435                 440                 445

Ala Lys Ile Ser Asp Phe Tyr Asn Thr Ile Gly Val His Pro Thr Ser
    450                 455                 460

Ala Glu Glu Leu Cys Ser Met Arg Thr Pro Ser Tyr Tyr Tyr Leu Lys
465                 470                 475                 480

Gly Glu Lys Met Glu Thr Leu Pro Glu Ser Ser Leu
                485                 490

<210> SEQ ID NO 11
<211> LENGTH: 492
<212> TYPE: PRT
<213> ORGANISM: Trypanosoma congolense

<400> SEQUENCE: 11

Met Ser Lys Ala Phe Asp Leu Val Ile Ile Gly Ala Gly Ser Gly Gly
1               5                   10                  15

Leu Glu Ala Gly Trp Asn Ala Ala Thr Leu Tyr Lys Lys Arg Val Ala
                20                  25                  30
```

```
Val Val Asp Val Gln Thr Val His Gly Pro Pro Phe Phe Ala Ala Leu
         35                  40                  45

Gly Gly Thr Cys Val Asn Val Gly Cys Val Pro Lys Lys Leu Met Val
 50                  55                  60

Thr Gly Ala Gln Tyr Met Asp Gln Leu Arg Glu Ser Ala Gly Phe Gly
 65                  70                  75                  80

Trp Glu Phe Asp Ala Ser Thr Ile Lys Ala Asn Trp Lys Thr Leu Ile
                 85                  90                  95

Ala Ala Lys Asn Ala Ala Val Leu Asp Ile Asn Lys Ser Tyr Glu Asp
                100                 105                 110

Met Phe Lys Asp Thr Glu Gly Leu Glu Phe Phe Leu Gly Trp Gly Ala
            115                 120                 125

Leu Glu Gln Lys Asn Val Val Thr Val Arg Glu Gly Ala Asp Pro Lys
        130                 135                 140

Ser Lys Val Lys Glu Arg Leu Gln Ala Glu His Ile Ile Ile Ala Thr
145                 150                 155                 160

Gly Ser Trp Pro Gln Met Leu Lys Ile Pro Gly Ile Glu His Cys Ile
                165                 170                 175

Ser Ser Asn Glu Ala Phe Tyr Leu Glu Glu Pro Arg Arg Val Leu
                180                 185                 190

Thr Val Gly Gly Gly Phe Ile Ser Val Glu Phe Ala Gly Ile Phe Asn
            195                 200                 205

Ala Tyr Lys Pro Val Gly Gly Lys Val Thr Leu Cys Tyr Arg Asn Asn
        210                 215                 220

Pro Ile Leu Arg Gly Phe Asp Tyr Thr Leu Arg Gln Glu Leu Thr Lys
225                 230                 235                 240

Gln Leu Val Ala Asn Gly Ile Asp Ile Met Thr Asn Glu Asn Pro Ser
                245                 250                 255

Lys Ile Glu Leu Asn Pro Asp Gly Ser Lys His Val Thr Phe Glu Ser
                260                 265                 270

Gly Lys Thr Leu Asp Val Asp Val Val Met Met Ala Ile Gly Arg Leu
            275                 280                 285

Pro Arg Thr Gly Tyr Leu Gln Leu Gln Thr Val Gly Val Asn Leu Thr
        290                 295                 300

Asp Lys Gly Ala Ile Gln Val Asp Glu Phe Ser Arg Thr Asn Val Pro
305                 310                 315                 320

Asn Ile Tyr Ala Ile Gly Asp Val Thr Gly Arg Ile Met Leu Thr Pro
                325                 330                 335

Val Ala Ile Asn Glu Gly Ala Ser Val Val Asp Thr Ile Phe Gly Ser
            340                 345                 350

Lys Pro Arg Lys Thr Asp His Thr Arg Val Ala Ser Ala Val Phe Ser
        355                 360                 365

Ile Pro Pro Ile Gly Thr Cys Gly Leu Thr Glu Glu Ala Ala Lys
        370                 375                 380

Ser Phe Glu Lys Val Ala Val Tyr Leu Ser Cys Phe Thr Pro Leu Met
385                 390                 395                 400

His Asn Ile Ser Gly Ser Lys Tyr Lys Lys Phe Val Ala Lys Ile Ile
                405                 410                 415

Thr Asp His Gly Asp Gly Thr Val Gly Val His Leu Leu Gly Asp
            420                 425                 430

Ser Ser Pro Glu Ile Ile Gln Ala Val Gly Ile Cys Met Lys Leu Asn
        435                 440                 445
```

```
Ala Lys Ile Ser Asp Phe Tyr Asn Thr Ile Gly Val His Pro Thr Ser
    450                 455                 460

Ala Glu Glu Leu Cys Ser Met Arg Thr Pro Ser His Tyr Tyr Ile Lys
465                 470                 475                 480

Gly Glu Lys Met Glu Thr Leu Pro Asp Ser Ser Leu
                485                 490

<210> SEQ ID NO 12
<211> LENGTH: 492
<212> TYPE: PRT
<213> ORGANISM: Trypanosoma cruzi

<400> SEQUENCE: 12

Met Met Ser Lys Ile Phe Asp Leu Val Val Ile Gly Ala Gly Ser Gly
1               5                   10                  15

Gly Leu Glu Ala Ala Trp Asn Ala Ala Thr Leu Tyr Lys Lys Arg Val
            20                  25                  30

Ala Val Ile Asp Val Gln Met His Gly Pro Pro Phe Phe Ser Ala
        35                  40                  45

Leu Gly Gly Thr Cys Val Asn Val Gly Cys Val Pro Lys Lys Leu Met
50                  55                  60

Val Thr Gly Ala Gln Tyr Met Glu His Leu Arg Glu Ser Ala Gly Phe
65                  70                  75                  80

Gly Trp Glu Phe Asp Arg Thr Thr Leu Arg Ala Glu Trp Lys Lys Leu
                85                  90                  95

Ile Ala Val Lys Asp Glu Ala Val Leu Asn Ile Asn Lys Ser Tyr Glu
            100                 105                 110

Glu Met Phe Arg Asp Thr Glu Gly Leu Glu Phe Phe Leu Gly Trp Gly
        115                 120                 125

Ser Leu Glu Ser Lys Asn Val Val Asn Val Arg Glu Ser Ala Asp Pro
130                 135                 140

Ala Ser Ala Val Lys Glu Arg Leu Glu Thr Glu Asn Ile Leu Leu Ala
145                 150                 155                 160

Ser Gly Ser Trp Pro His Met Pro Asn Ile Pro Gly Ile Glu His Cys
                165                 170                 175

Ile Ser Ser Asn Glu Ala Phe Tyr Leu Pro Glu Pro Arg Arg Val
            180                 185                 190

Leu Thr Val Gly Gly Gly Phe Ile Ser Val Glu Phe Ala Gly Ile Phe
        195                 200                 205

Asn Ala Tyr Lys Pro Lys Asp Gly Gln Val Thr Leu Cys Tyr Arg Gly
210                 215                 220

Glu Met Ile Leu Arg Gly Phe Asp His Thr Leu Arg Glu Glu Leu Thr
225                 230                 235                 240

Lys Gln Leu Thr Ala Asn Gly Ile Gln Ile Leu Thr Lys Glu Asn Pro
                245                 250                 255

Ala Lys Val Glu Leu Asn Ala Asp Gly Ser Lys Ser Val Thr Phe Glu
            260                 265                 270

Ser Gly Lys Lys Met Asp Phe Asp Leu Val Met Met Ala Ile Gly Arg
        275                 280                 285

Ser Pro Arg Thr Lys Asp Leu Gln Leu Gln Asn Ala Gly Val Met Ile
290                 295                 300

Lys Asn Gly Gly Val Gln Val Asp Glu Tyr Ser Arg Thr Asn Val Ser
305                 310                 315                 320

Asn Ile Tyr Ala Ile Gly Asp Val Thr Asn Arg Val Met Leu Thr Pro
                325                 330                 335
```

```
Val Ala Ile Asn Glu Ala Ala Ala Leu Val Asp Thr Val Phe Gly Thr
            340                 345                 350

Asn Pro Arg Lys Thr Asp His Thr Arg Val Ala Ser Ala Val Phe Ser
            355                 360                 365

Ile Pro Pro Ile Gly Thr Cys Gly Leu Ile Glu Glu Val Ala Ser Lys
        370                 375                 380

Arg Tyr Glu Val Val Ala Val Tyr Leu Ser Ser Phe Thr Pro Leu Met
385                 390                 395                 400

His Asn Ile Ser Gly Ser Lys Tyr Lys Thr Phe Val Ala Lys Ile Ile
                405                 410                 415

Thr Asn His Ser Asp Gly Thr Val Leu Gly Val His Leu Leu Gly Asp
                420                 425                 430

Asn Ala Pro Glu Ile Ile Gln Gly Val Gly Ile Cys Leu Lys Leu Asn
            435                 440                 445

Ala Lys Ile Ser Asp Phe Tyr Asn Thr Ile Gly Val His Pro Thr Ser
450                 455                 460

Ala Glu Glu Leu Cys Ser Met Arg Thr Pro Ser Tyr Tyr Tyr Val Lys
465                 470                 475                 480

Gly Glu Lys Met Glu Lys Pro Ser Glu Ala Ser Leu
                485                 490
```